(12) United States Patent
Arnett et al.

(10) Patent No.: US 9,615,856 B2
(45) Date of Patent: Apr. 11, 2017

(54) SACROILIAC FUSION CAGE

(71) Applicant: IMDS LLC, Providence, UT (US)

(72) Inventors: Jeffery D. Arnett, Gilbert, AZ (US);
Joshua A. Butters, Chandler, AZ (US);
Dylan M. Hushka, Gilbert, AZ (US);
Nicholas Slater, Chandler, AZ (US);
Daniel J. Triplett, Providence, UT
(US); David A. Rupp, Hyde Park, UT
(US); Jared M. White, Salt Lake City,
UT (US); Karen E. Mohr, Salt Lake
City, UT (US)

(73) Assignee: IMDS LLC, Providence, UT (US)

( * ) Notice: Subject to any disclaimer, the term of this patent is extended or adjusted under 35 U.S.C. 154(b) by 255 days.

(21) Appl. No.: 13/666,956

(22) Filed: Nov. 1, 2012

(65) Prior Publication Data

US 2013/0144343 A1   Jun. 6, 2013

Related U.S. Application Data

(60) Provisional application No. 61/554,395, filed on Nov. 1, 2011.

(51) Int. Cl.
*A61B 17/88* (2006.01)
*A61B 17/70* (2006.01)
*A61B 17/064* (2006.01)

(52) U.S. Cl.
CPC .......... *A61B 17/70* (2013.01); *A61B 17/0642* (2013.01); *A61B 17/7055* (2013.01); *A61B 2017/0641* (2013.01)

(58) Field of Classification Search
CPC .......... A61F 2/4455; A61F 2002/30622; A61F 2002/30995; A61B 17/7055; A61B 17/1671; A61B 17/68; A61B 17/8685; A61B 17/1664; A61B 17/846; A61B 17/844; A61B 17/8645; A61B 17/1739
USPC ................... 606/246, 279; 623/17.11–17.16
See application file for complete search history.

(56) References Cited

U.S. PATENT DOCUMENTS

| | | |
|---|---|---|
| 3,486,505 A | 12/1969 | Morrison |
| 3,641,590 A | 2/1972 | Michele |
| 3,650,309 A | 3/1972 | Neuschotz |
| 3,842,825 A | 10/1974 | Wagner |
| 3,848,276 A | 11/1974 | Martinez |
| 3,882,917 A | 5/1975 | Orlomoski |
| 3,896,504 A | 7/1975 | Fischer |
| 3,907,017 A | 9/1975 | Stanwick |
| 3,927,503 A | 12/1975 | Wilson |
| 4,011,602 A | 3/1977 | Rybicki |
| 4,047,524 A | 9/1977 | Hall |
| 4,260,005 A | 4/1981 | Stencel |
| 4,349,955 A | 9/1982 | Keen |

(Continued)

FOREIGN PATENT DOCUMENTS

| | | |
|---|---|---|
| EP | 179695 A1 | 4/1986 |
| WO | WO03053290 A1 | 7/2003 |

(Continued)

*Primary Examiner* — Lynnsy Summitt
(74) *Attorney, Agent, or Firm* — David L. Stott

(57) ABSTRACT

Devices for sacroiliac joint fusion may be implanted from an anterior, posterior, or lateral approach. Multiple devices may be used in a single fusion procedure. Some examples include blade anchors which extend from a central beam, pin, cage, or body.

17 Claims, 28 Drawing Sheets

(56) References Cited

U.S. PATENT DOCUMENTS

| | | |
|---|---|---|
| 4,355,429 A | 10/1982 | Mittelmeier |
| 4,484,570 A | 11/1984 | Sutter |
| 4,501,269 A | 2/1985 | Bagby |
| 4,611,581 A | 9/1986 | Steffee |
| 4,642,869 A | 2/1987 | Muller |
| 4,716,893 A | 1/1988 | Fischer |
| 4,764,067 A | 8/1988 | Kawashima |
| 4,820,305 A | 4/1989 | Harms |
| 4,834,757 A | 5/1989 | Brantigan |
| 4,838,891 A | 6/1989 | Branemark |
| 4,865,607 A | 9/1989 | Witzel |
| 4,874,389 A | 10/1989 | Downey |
| 4,930,962 A | 6/1990 | Reynolds |
| 4,946,378 A | 8/1990 | Hirayama |
| 4,957,496 A | 9/1990 | Schmidt |
| 5,002,576 A | 3/1991 | Fuhrmann |
| 5,019,103 A | 5/1991 | Van |
| 5,074,880 A | 12/1991 | Mansat |
| 5,147,361 A | 9/1992 | Ojima |
| 5,163,960 A | 11/1992 | Bonutti |
| 5,192,324 A | 3/1993 | Kenna |
| 5,192,327 A | 3/1993 | Brantigan |
| 5,306,309 A | 4/1994 | Wagner |
| 5,314,477 A | 5/1994 | Marnay |
| 5,431,658 A | 7/1995 | Moskovich |
| 5,443,515 A | 8/1995 | Cohen |
| D364,462 S | 11/1995 | Michelson |
| 5,507,816 A | 4/1996 | Bullivant |
| 5,514,180 A | 5/1996 | Heggeness |
| D378,409 S | 3/1997 | Michelson |
| 5,609,635 A | 3/1997 | Michelson |
| 5,658,337 A | 8/1997 | Kohrs |
| 5,683,394 A | 11/1997 | Rinner |
| 5,702,449 A | 12/1997 | McKay |
| 5,709,683 A | 1/1998 | Bagby |
| 5,713,899 A | 2/1998 | Marnay |
| 5,769,852 A | 6/1998 | Branemark |
| 5,788,701 A | 8/1998 | McCue |
| 5,800,550 A | 9/1998 | Sertich |
| 5,853,414 A | 12/1998 | Groiso |
| 5,893,889 A | 4/1999 | Harrington |
| 5,893,890 A | 4/1999 | Pisharodi |
| 5,993,476 A | 11/1999 | Groiso |
| 6,053,916 A * | 4/2000 | Moore ............... A61F 2/30988 606/86 R |
| 6,063,121 A | 5/2000 | Xavier |
| 6,096,080 A | 8/2000 | Nicholson |
| 6,102,949 A | 8/2000 | Biedermann |
| 6,113,638 A | 9/2000 | Williams |
| 6,235,059 B1 | 5/2001 | Benezech |
| 6,325,805 B1 | 12/2001 | Ogilvie |
| 6,336,928 B1 | 1/2002 | Guerin |
| 6,402,785 B1 | 6/2002 | Zdeblick |
| 6,413,278 B1 | 7/2002 | Marchosky |
| 6,432,107 B1 | 8/2002 | Ferree |
| 6,447,524 B1 | 9/2002 | Knodel |
| 6,447,546 B1 | 9/2002 | Bramlet |
| 6,458,159 B1 | 10/2002 | Thalgott |
| 6,558,424 B2 | 5/2003 | Thalgott |
| 6,582,468 B1 | 6/2003 | Gauchet |
| 6,610,093 B1 | 8/2003 | Pisharodi |
| 6,620,198 B2 | 9/2003 | Burstein |
| 6,652,533 B2 | 11/2003 | O'Neil |
| 6,716,245 B2 | 4/2004 | Pasquet |
| 6,726,720 B2 | 4/2004 | Ross |
| 6,740,118 B2 | 5/2004 | Eisermann |
| 6,743,256 B2 | 6/2004 | Mason |
| 6,755,841 B2 | 6/2004 | Fraser |
| 6,770,096 B2 | 8/2004 | Bolger |
| 6,802,863 B2 | 10/2004 | Lawson |
| 6,969,390 B2 | 11/2005 | Michelson |
| 6,972,035 B2 | 12/2005 | Michelson |
| 7,041,135 B2 | 5/2006 | Michelson |
| 7,044,972 B2 | 5/2006 | Mathys, Jr. |
| 7,048,766 B2 | 5/2006 | Ferree |
| 7,056,344 B2 | 6/2006 | Huppert |
| 7,056,345 B2 | 6/2006 | Kuslich |
| 7,060,097 B2 | 6/2006 | Fraser |
| 7,083,623 B2 | 8/2006 | Michelson |
| 7,083,652 B2 | 8/2006 | McCue |
| 7,115,146 B2 | 10/2006 | Boyer, II |
| 7,118,580 B1 | 10/2006 | Beyersdorff |
| 7,128,761 B2 | 10/2006 | Kuras |
| 7,166,110 B2 | 1/2007 | Yundt |
| 7,166,129 B2 | 1/2007 | Michelson |
| 7,169,182 B2 | 1/2007 | Errico |
| 7,204,852 B2 | 4/2007 | Marnay |
| 7,235,105 B2 | 6/2007 | Jackson |
| 7,320,707 B2 | 1/2008 | Zucherman |
| 7,326,248 B2 | 2/2008 | Michelson |
| 7,357,817 B2 | 4/2008 | D'Alessio, II |
| 7,396,365 B2 | 7/2008 | Michelson |
| 7,481,830 B2 | 1/2009 | Wall |
| 7,503,935 B2 | 3/2009 | Zucherman |
| D594,986 S | 6/2009 | Miles |
| 7,540,882 B2 | 6/2009 | Michelson |
| 7,556,650 B2 | 7/2009 | Collins |
| 7,572,293 B2 | 8/2009 | Rhodes |
| 7,588,600 B2 | 9/2009 | Benzel |
| 7,594,931 B2 | 9/2009 | Louis |
| 7,611,538 B2 | 11/2009 | Belliard |
| 7,658,766 B2 | 2/2010 | Melkent |
| 7,695,516 B2 | 4/2010 | Zeegers |
| 7,749,271 B2 | 7/2010 | Fischer |
| 7,763,076 B2 | 7/2010 | Navarro |
| 7,780,676 B2 | 8/2010 | Lakin |
| 7,837,732 B2 | 11/2010 | Zucherman |
| 7,922,765 B2 * | 4/2011 | Reiley ............... A61B 17/1615 606/279 |
| 8,021,403 B2 | 9/2011 | Wall |
| 8,034,076 B2 | 10/2011 | Criscuolo |
| 8,100,974 B2 | 1/2012 | Duggal |
| 8,105,389 B2 | 1/2012 | Berelsman |
| 8,133,283 B2 | 3/2012 | Wilson |
| 8,157,865 B2 | 4/2012 | Hochschuler |
| 8,287,572 B2 * | 10/2012 | Bae ............... A61B 17/846 606/279 |
| 8,349,015 B2 | 1/2013 | Bae et al. |
| 8,388,667 B2 * | 3/2013 | Reiley ............... A61B 17/68 606/300 |
| 8,821,555 B2 | 9/2014 | Bae et al. |
| 9,033,993 B2 | 5/2015 | Bae et al. |
| 9,138,275 B2 | 9/2015 | Bae et al. |
| 9,138,276 B2 | 9/2015 | Bae et al. |
| 2002/0035400 A1 | 3/2002 | Bryan |
| 2002/0049447 A1 | 4/2002 | Li |
| 2002/0116165 A1 | 8/2002 | El-Ghoroury |
| 2002/0147454 A1 | 10/2002 | Neto |
| 2002/0147499 A1 | 10/2002 | Shea |
| 2002/0165613 A1 | 11/2002 | Lin |
| 2003/0045940 A1 | 3/2003 | Eberlein |
| 2003/0060884 A1 | 3/2003 | Fell |
| 2003/0195517 A1 | 10/2003 | Michelson |
| 2003/0195632 A1 | 10/2003 | Foley |
| 2004/0030336 A1 | 2/2004 | Khanna |
| 2004/0030339 A1 | 2/2004 | Wack |
| 2004/0073315 A1 | 4/2004 | Justin |
| 2004/0083005 A1 | 4/2004 | Jacobsson |
| 2004/0148028 A1 | 7/2004 | Ferree |
| 2004/0176853 A1 | 9/2004 | Sennett |
| 2004/0199254 A1 | 10/2004 | Louis |
| 2004/0220670 A1 | 11/2004 | Eisermann |
| 2004/0254581 A1 | 12/2004 | Leclair |
| 2005/0004672 A1 | 1/2005 | Pafford |
| 2005/0014919 A1 | 1/2005 | Hatakeyama |
| 2005/0149192 A1 | 7/2005 | Zucherman |
| 2005/0165408 A1 | 7/2005 | Puno |
| 2005/0171607 A1 | 8/2005 | Michelson |
| 2005/0177239 A1 | 8/2005 | Steinberg |
| 2005/0192586 A1 | 9/2005 | Zucherman |
| 2005/0216089 A1 | 9/2005 | Michelson |
| 2005/0273108 A1 | 12/2005 | Groiso |
| 2006/0004453 A1 | 1/2006 | Bartish |
| 2006/0074421 A1 | 4/2006 | Bickley |

(56) References Cited

U.S. PATENT DOCUMENTS

| | | |
|---|---|---|
| 2006/0085071 A1 | 4/2006 | Lechmann |
| 2006/0095136 A1 | 5/2006 | McLuen |
| 2006/0111787 A1 | 5/2006 | Bailie |
| 2006/0116769 A1 | 6/2006 | Marnay |
| 2006/0129238 A1 | 6/2006 | Paltzer |
| 2006/0167461 A1 | 7/2006 | Hawkins |
| 2006/0178745 A1 | 8/2006 | Bartish |
| 2006/0241641 A1 | 10/2006 | Albans |
| 2007/0010890 A1 | 1/2007 | Collazo |
| 2007/0050032 A1 | 3/2007 | Gittings |
| 2007/0055376 A1 | 3/2007 | Michelson |
| 2007/0073404 A1 | 3/2007 | Rashbaum |
| 2007/0106388 A1 | 5/2007 | Michelson |
| 2007/0118145 A1 | 5/2007 | Fischer |
| 2007/0123903 A1 | 5/2007 | Raymond |
| 2007/0142922 A1 | 6/2007 | Lewis |
| 2007/0156241 A1* | 7/2007 | Reiley ............... A61B 17/1615 623/17.11 |
| 2007/0185375 A1 | 8/2007 | Stad |
| 2007/0233244 A1 | 10/2007 | Lopez |
| 2007/0239278 A1 | 10/2007 | Heinz |
| 2007/0288005 A1 | 12/2007 | Arnin |
| 2007/0288021 A1 | 12/2007 | Rickels |
| 2007/0299529 A1 | 12/2007 | Rhodes |
| 2008/0015702 A1 | 1/2008 | Lakin |
| 2008/0051901 A1 | 2/2008 | De Villiers |
| 2008/0103598 A1 | 5/2008 | Trudeau |
| 2008/0132949 A1 | 6/2008 | Aferzon |
| 2008/0147203 A1 | 6/2008 | Cornin |
| 2008/0154377 A1 | 6/2008 | Voellmicke |
| 2008/0177275 A1 | 7/2008 | Wing |
| 2008/0208345 A1 | 8/2008 | Hurlbert |
| 2008/0249575 A1 | 10/2008 | Waugh |
| 2008/0249623 A1 | 10/2008 | Bao |
| 2008/0275455 A1 | 11/2008 | Berry |
| 2008/0287957 A1 | 11/2008 | Hester |
| 2009/0005784 A1 | 1/2009 | Blain |
| 2009/0005870 A1 | 1/2009 | Hawkins |
| 2009/0048604 A1 | 2/2009 | Milz |
| 2009/0062921 A1 | 3/2009 | Michelson |
| 2009/0088849 A1 | 4/2009 | Armstrong |
| 2009/0099601 A1 | 4/2009 | Aferzon |
| 2009/0099602 A1 | 4/2009 | Aflatoon |
| 2009/0138015 A1* | 5/2009 | Conner ............... A61B 17/1615 606/80 |
| 2009/0164020 A1 | 6/2009 | Janowski |
| 2009/0209967 A1 | 8/2009 | Evans |
| 2009/0259261 A1* | 10/2009 | Reiley ............... A61B 17/8897 606/329 |
| 2010/0004747 A1 | 1/2010 | Lin |
| 2010/0185292 A1* | 7/2010 | Hochschuler ......... A61F 2/4455 623/17.16 |
| 2010/0201739 A1 | 8/2010 | Yamaguchi |
| 2010/0204739 A1 | 8/2010 | Bae |
| 2010/0268228 A1* | 10/2010 | Petersen ............. A61F 2/30988 606/60 |
| 2011/0264229 A1* | 10/2011 | Donner ............... A61F 2/30988 623/18.11 |
| 2012/0083883 A1* | 4/2012 | Ginn ................ A61B 17/1604 623/17.11 |
| 2012/0095560 A1* | 4/2012 | Donner ............... A61F 2/30988 623/17.11 |
| 2014/0135927 A1* | 5/2014 | Pavlov ............... A61B 17/7055 623/17.11 |
| 2015/0223951 A1 | 8/2015 | Bae et al. |
| 2016/0000578 A1 | 1/2016 | Bae et al. |

FOREIGN PATENT DOCUMENTS

| | | |
|---|---|---|
| WO | WO2004071359 A2 | 8/2004 |
| WO | WO2005051243 A2 | 6/2005 |
| WO | WO2005074841 A1 | 8/2005 |
| WO | WO2006051547 A2 | 5/2006 |
| WO | WO2006074414 A2 | 7/2006 |
| WO | WO2006086494 A2 | 8/2006 |
| WO | WO2007087366 A2 | 8/2007 |
| WO | WO2008014258 A2 | 1/2008 |
| WO | WO2008021955 A2 | 2/2008 |
| WO | WO2008128367 A1 | 10/2008 |
| WO | WO2010039026 | 4/2010 |
| WO | WO2011044879 | 4/2011 |
| WO | WO2011090508 A1 | 7/2011 |

* cited by examiner

SACROILIAC FUSION CAGE

CROSS-REFERENCE TO RELATED APPLICATIONS

This application is a non-provisional of:

U.S. Provisional Patent Application No. 61/554,395, filed Nov. 1, 2011 and entitled SACROILIAC FUSION CAGE.

The above-identified document is herein incorporated by reference in its entirety.

BACKGROUND OF THE DISCLOSURE

The present disclosure relates to embodiments of blade anchor fusion devices that may be used to fuse the bones of the sacroiliac joint, specifically the sacrum and ilium. It will be appreciated that any of the disclosed embodiments may have application outside of sacroiliac joint fusion applications, and may be used to provide compression across a fusion or fracture line in any application where a typical fusion device or bone staple may be used. It will also be appreciated that any of the below named embodiments can be mixed and matched to form alternate embodiments.

An example of the present technology is concerned with fusion of the sacroiliac joint by blade anchors that extend outward from a central cage. The blade anchors may be secured to opposite sides of the sacroiliac joint to compress the joint and facilitate fusion.

Those of skill in the art will recognize that the following description is merely illustrative of the principles of the disclosure, which may be applied in various ways to provide many different alternative embodiments and may be applicable outside the fields of surgery or medical devices. While the present disclosure is made in the context of fusing the sacroiliac joint for the purposes of illustrating the concepts of the design, it is contemplated that the present design and/or variations thereof may be suited to other uses, such as fusing other joints in the human body, or to stabilize bone fractures, etc. Moreover, the implants, instrumentation and methods set forth herein may be used in open, percutaneous, and/or minimally invasive procedures.

All changes which come within the meaning and range of equivalency of the claims are to be embraced within their scope.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

SUMMARY

In an embodiment, a method for sacroiliac joint fusion includes establishing an implant trajectory that passes through the sacroiliac joint; forming a tunnel along the implant trajectory, wherein an iliac portion of the tunnel passes through an iliac bone, wherein a sacral portion of the tunnel passes through a sacral bone; and inserting a fusion device along the implant trajectory so that an iliac portion of the fusion device is positioned in the iliac portion of the tunnel and a sacral portion of the fusion device is positioned in the sacral portion of the tunnel; wherein the fusion device includes a plurality of anchors extending beyond the tunnel.

In an embodiment, forming the tunnel includes cutting through the sacrum and ilium with the fusion device.

In an embodiment, inserting the fusion device includes inserting a body of the fusion device into the tunnel, inserting a first anchor into the body so that a portion of the anchor extends through a wall of the tunnel, and inserting a second anchor into the body so that a portion of the second anchor extends through a wall of the tunnel.

In an embodiment, a second fusion device is inserted along a second implant trajectory so that the second fusion device engages iliac and sacral bone.

In an embodiment, inserting the fusion device includes compressing the ilium and the sacrum together with the fusion device.

In an embodiment, inserting the fusion device includes inserting a first body of the fusion device into the tunnel so that a first blade connected to the first body penetrates through a wall of the tunnel, and inserting a second body of the fusion device into the first body so that a second blade connected to the second body penetrates through the wall of the tunnel.

BRIEF DESCRIPTION OF THE DRAWINGS

Various embodiments of the present disclosure will now be discussed with reference to the appended drawings. It will be appreciated that these drawings depict only typical examples of the present disclosure and are therefore not to be considered limiting of its scope.

DETAILED DESCRIPTION

While certain embodiments are shown and described in detail below by way of illustration only, it will be clear to the person skilled in the art upon reading and understanding this disclosure that changes, modifications, and variations may be made and remain within the scope of the technology described herein. Furthermore, while various features are grouped together in the embodiments for the purpose of streamlining the disclosure, it is appreciated that features from different embodiments may be combined to form additional embodiments which are all contemplated within the scope of the disclosed technology.

Not every feature of each embodiment is labeled in every figure in which that embodiment appears, in order to keep the figures clear. Similar reference numbers (for example, those that are identical except for the first numeral) may be used to indicate similar features in different embodiments.

Any of the devices described herein may be fabricated from metals, alloys, polymers, plastics, ceramics, glasses, composite materials, or combinations thereof, including but not limited to: polyether ether ketone (PEEK), commercially pure titanium, titanium alloys, ASTM F67, Nitinol, cobalt chrome, cobalt chrome alloys, stainless steel, ultra-high molecular-weight polyethylene (UHMWPE) and biodegradable materials, among others. Different materials may be used within a single part. The implants disclosed herein may also encompass a variety of surface treatments or additives to encourage bony attachment, including but not limited to: porous coatings, hydroxyapatite, tricalcium phosphate (TCP), anti-microbial additives, analgesics, anti-inflammatories, bone morphogenic proteins (BMPs), phorbol myristate acetate (PMA), bone growth promoting material, poly-L-lactide (PLLA), polyglycolide (PGA), tricalcium phosphate (TCP), demineralized bone, cancellous bone chips, etc. Any implant disclosed herein may include a radiographic marker for imaging purposes. Any implant disclosed herein may be colored, coded or otherwise marked to make it easier for the surgeon to identify the type and size of the implant.

Figure 1:
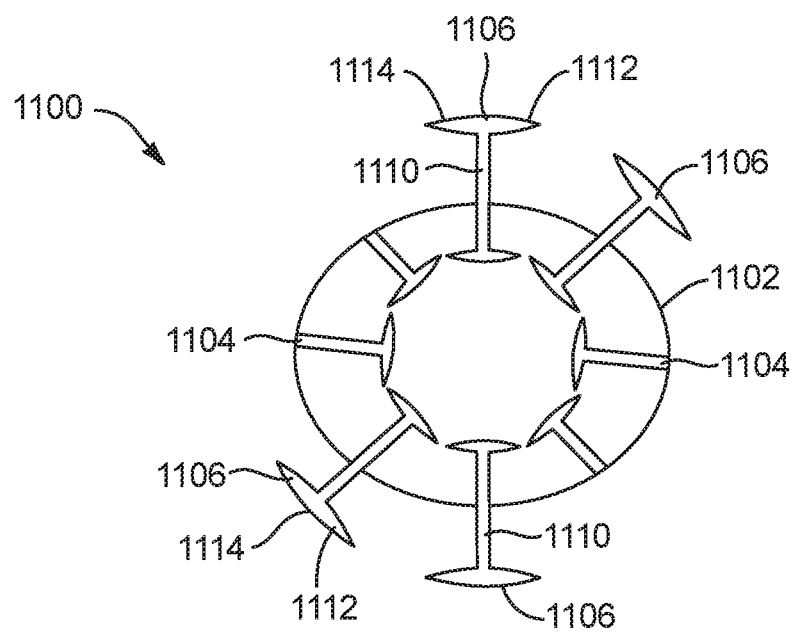
FIG. 1 is a top view of a fusion device with a body and anchors.

FIG. 1 illustrates a device that may be used for fusion of the sacroiliac joint. Fusion device 1100 may include a cylindrical cage 1102 with a plurality of dovetail slots 1104. Throughout this disclosure, dovetail slots may be referred to as dovetails. The example of FIG. 1 includes eight dovetail slots 1104 which are evenly spaced around a generally circular perimeter of the cage 1102. The dovetail slots 1104 may be shaped to receive anchors 1106, fins, teeth or other fixation features that may extend radially from the cage 1102. FIG. 1 shows anchors 1106 that extend radially outward from the cage 1102. The anchors 1106 may include an arm 1110 and a blade 1112 that is perpendicular to the arm 1110, forming a T shape. The length of the arm 1110 may vary, and the size, shape, and orientation or angulation of the blade 1112 may also be variable. The blade 1112 may include a smooth outer surface 1114 that is oriented away from the cage 1102, or the outer surface 1114 may contain additional texture, for example, teeth or ridges to enhance fixation.

The anchors 1106 may be integrally formed with the cylindrical cage 1102, or may be formed separately and be connected to the cage 1102 via a rail, a snap, a clip or other connecting mechanism. FIG. 1 illustrates an example in which the anchors 1106 are formed separately so that anchors may be connected to the cage 1102 where needed. The anchors 1106 may be in a fixed position relative to the cage 1102, or may be axially moveable, for example, along a central longitudinal axis of the cage. The number of dovetails 1104 and corresponding anchors 1106 may be variable to accommodate various patient anatomies. There may be more dovetails 1104 than anchors 1106 used, as shown in FIG. 1.

The anchors 1106 and others disclosed herein may share some or all of the characteristics of the bone anchors disclosed in U.S. patent application Ser. No. 12/640,892, which is incorporated herein in its entirety.

Figure 10:
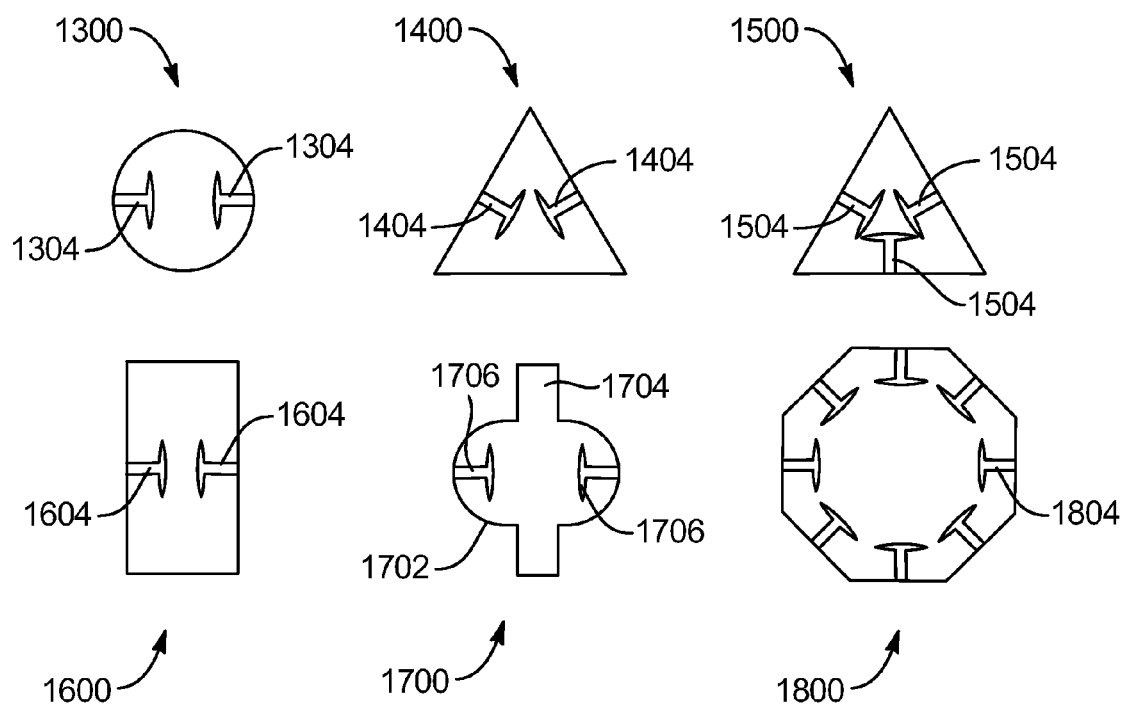
FIG. 10 is an end view of several fusion devices, each having a different profile.

With reference to FIG. 10, the geometry of the cage may vary. For example, an end view (or cross section) of the cage may be circular, triangular, rectangular, polygonal or irregularly shaped. FIG. 10 illustrates end views of a round cage 1300, two triangular cages 1400, 1500, a rectangular cage 1600, a cage 1700 with a profile formed of an oval 1702 superimposed on a rectangle 1704, and an octagonal cage 1800. Cages 1300, 1400, 1600, and 1700 each have two dovetails 1304, 1404, 1604, 1706, respectively. Cage 1500 is shown with three dovetails 1504, one in each side. Cage 1800 is also shown with one dovetail 1804 in each side. Other examples of cages may include a greater or lesser number of dovetails. The dovetails may be located at vertices of the cage cross sectional profile, on flat sides, or along curved surfaces. The dovetails may be symmetrically or asymmetrically located on the cage, and may be regularly or variably spaced apart from one another.

Figure 2:
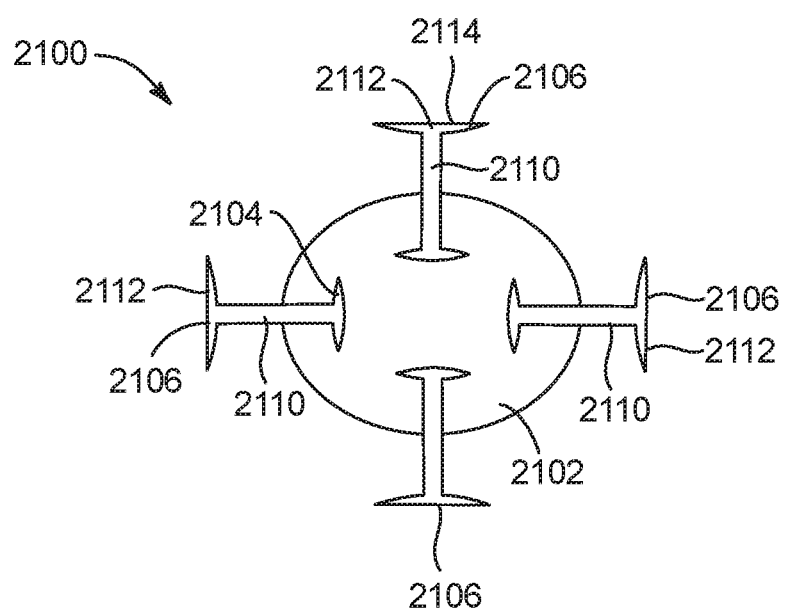
FIG. 2 is a top view of another fusion device, with another arrangement of anchors.

Referring to FIG. 2, another fusion device 2100 may include a cylindrical cage 2102 with a plurality of dovetail slots 2104. The example of FIG. 2 includes four dovetail slots 2104, which are evenly spaced around a circular perimeter of the cage 2102. The dovetail slots 2104 may be shaped to receive anchors 2106, fins, teeth or other fixation features that may extend radially from the cage 2102. FIG. 2 shows four anchors 2106 that extend radially outward from the cage 2102. The anchors 2106 may include an arm 2110 and a blade 2112 that is perpendicular to the arm 2110, forming a T shape. Other angles between the arm and blade are contemplated. The length of the arm 2110 may vary, and the size, shape, and orientation or angulation of the blade 2112 may also be variable. The blade 2112 may include a smooth outer surface 2114 that is oriented away from the cage 2102, or the outer surface 2114 may contain additional texture, for example, teeth or ridges to enhance fixation.

Figure 3:
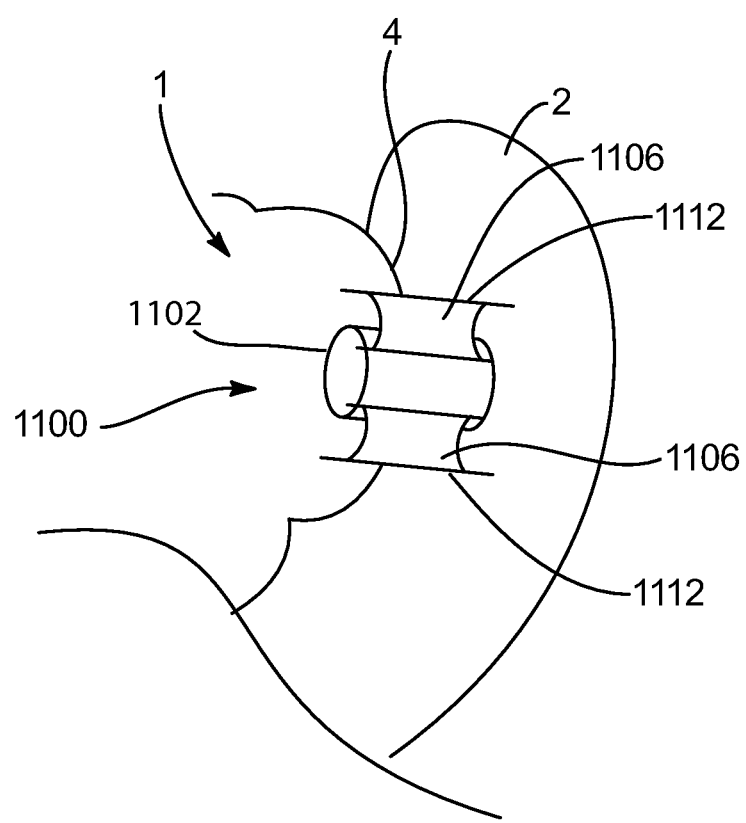
FIG. 3 is an anterior-posterior view of portions of a sacrum and ilium, with the fusion device of FIG. 1 implanted across the sacroiliac joint in a medial-lateral direction.

Referring to FIG. 3, the device 1100 may be placed such that the cage 1102 and each of the anchors 1106 extend medial-laterally across a sacroiliac joint 4 between a sacrum 1 and an ilium 2. In this orientation, a central axis of the cage 1102 may intersect the space of the sacroiliac joint. The anchors 1106 may also extend across the sacroiliac joint, with each anchor at least partially embedded within both the sacrum and the ilium. The device 1100 may be implanted from a lateral approach to achieve the illustrated orientation relative to the joint 4.

Alternatively, a fusion device may be inserted through a posterior or an anterior approach such that a central longitudinal axis of a cage of the device lies generally parallel to the sacroiliac joint space 4 and each individual blade may engage only one of the bones, either the sacrum 1 or the ilium 2.

Figure 4:
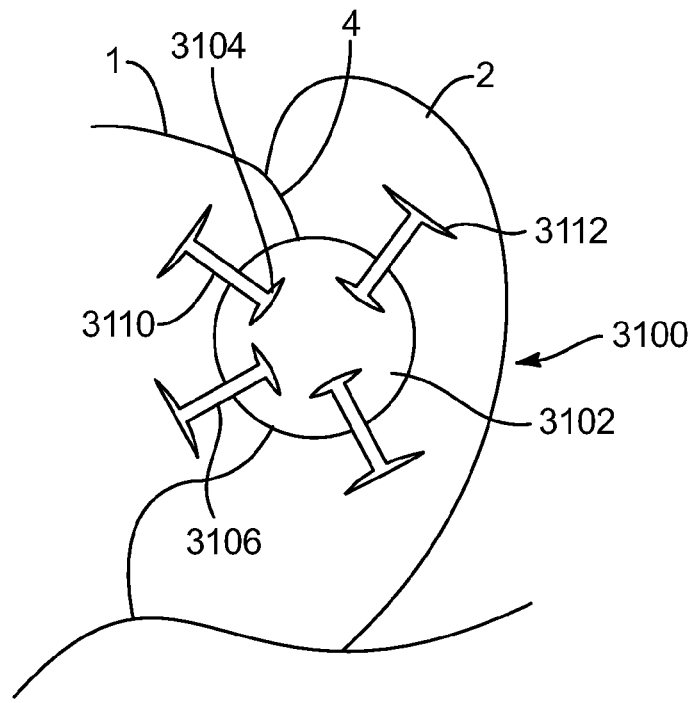
FIG. 4 is an anterior-posterior view of portions of a sacrum and ilium, with yet another fusion device implanted along the sacroiliac joint in an anterior-posterior direction, the fusion device having yet another arrangement of anchors.

FIG. 4 illustrates yet another fusion device 3100, which may be similar to fusion device 2100. Device 3100 includes a cylindrical cage 3102 with four dovetail slots 3104 which are asymmetrically or irregularly distributed around a circular perimeter of the cage 3102. Device 3100 also includes four anchors 3106, each with a blade 3112. In this embodiment, the anchors 3106 may provide compression of the joint to ensure fusion. This may be accomplished by configuring the cage 3102 and/or anchors 3106 so that, at a leading end of the device 3100, the blades 3112 diverge away from a central longitudinal axis of the cage 3102 and converge toward the central longitudinal axis at a trailing end of the device.

Figure 5:
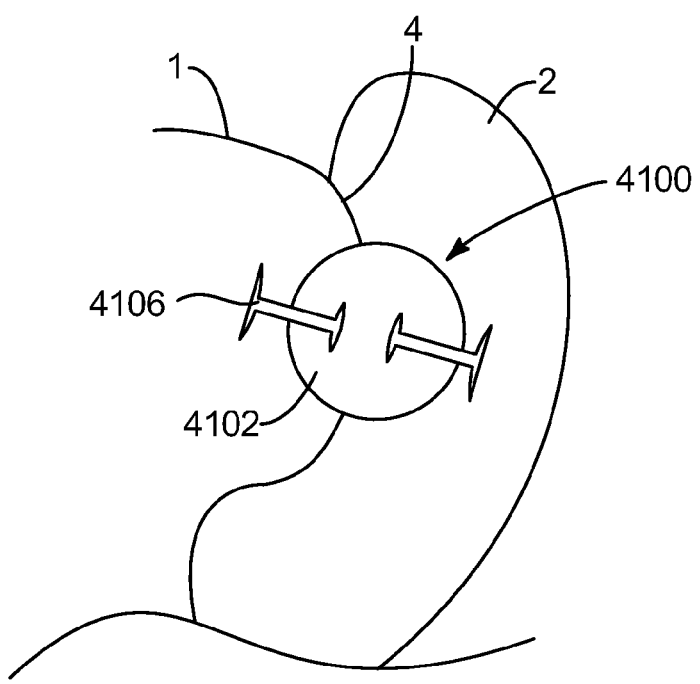
FIG. 5 is an anterior-posterior view of portions of a sacrum and ilium, with yet another fusion device implanted along the sacroiliac joint in an anterior-posterior direction, the fusion device having yet another arrangement of anchors.

FIG. 5 illustrates yet another fusion device 4100, which may be similar to any one of the foregoing fusion devices 1100, 2100, or 3100, at least in examples including two anchors on opposite sides of the cage. Fusion device 4100 includes a generally cylindrical cage 4102 and two anchors 4106 on opposite sides of the cage. Fusion device 4100 may be implanted from an anterior or posterior approach so that a central longitudinal axis of the device 4100 lies generally parallel to the joint line 4 between the sacrum 1 and the ilium 2. The anchors 4106 may provide compression across the joint as described for FIG. 4.

Figure 6:
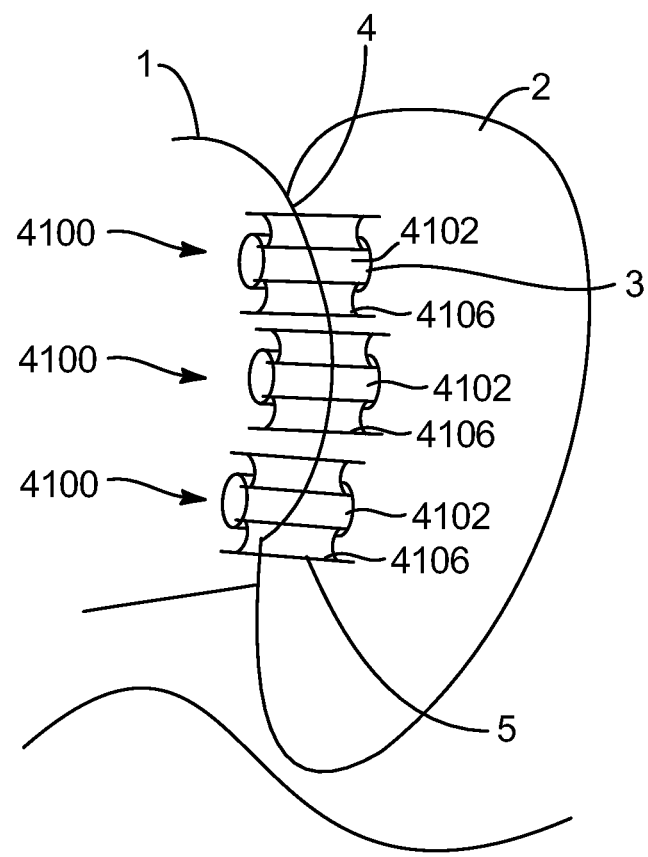
FIG. 6 is an anterior-posterior view of portions of a sacrum and ilium, with several fusion devices of FIG. 5 implanted across the sacroiliac joint, each device oriented in a medial-lateral direction.

Referring to FIG. 6, multiple fusion devices may be implanted from a lateral approach to extend across a sacroiliac joint line 4. FIG. 6 illustrates this principle with device 4100. The devices 4100 may lie adjacent to each other in a generally linear or curved array, or may be arranged in rows and columns. Each of the devices 4100 may be oriented with a central longitudinal axis of the device intersecting the joint 4. Other fusion devices in this disclosure may be implanted similarly.

Figure 7:
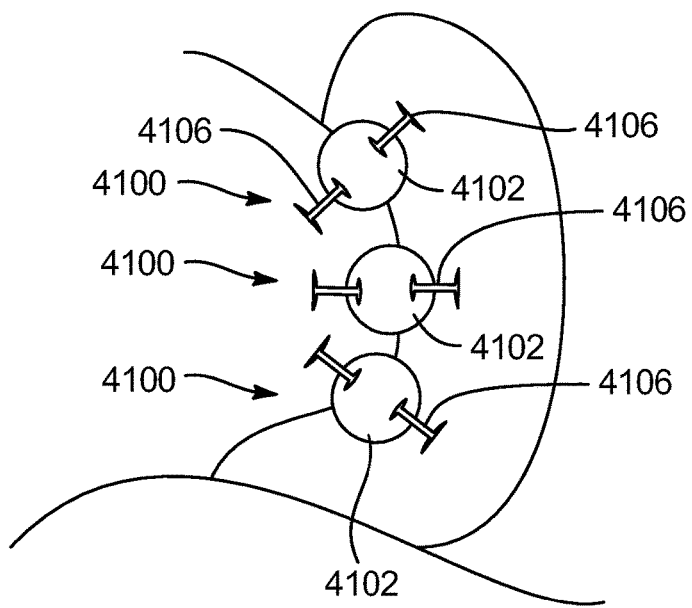
FIG. 7 is an anterior-posterior view of portions of a sacrum and ilium, with several fusion devices of FIG. 5 implanted along the sacroiliac joint, each device oriented in an anterior-posterior direction.

Referring to FIG. 7, multiple fusion devices may be implanted from an anterior or posterior approach to extend generally parallel to a sacroiliac joint line 4, or in other words, to extend along the joint space. FIG. 7 illustrates this principle with device 4100. The devices 4100 may lie adjacent to each other in a generally linear or curved array according to the geometry of the joint line. This arrangement may provide compression across the joint 4, similar to that described above for FIGS. 4-5. Other fusion devices in this disclosure may be implanted similarly.

Figures 8A, 8B:
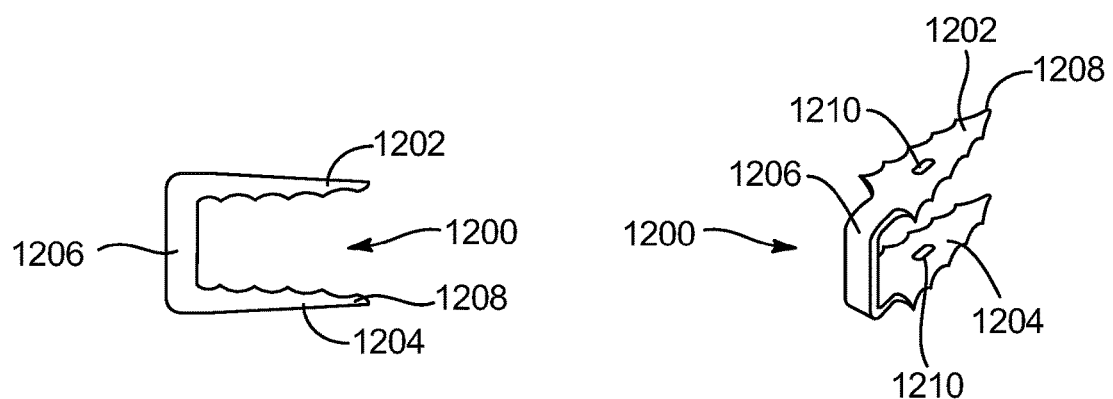
FIG. 8A is a side view of yet another fusion device.
FIG. 8B is an oblique view of the fusion device of FIG. 8A.

Referring to FIGS. 8A-8B, yet another fusion device 1200 may be essentially U shaped so as to resemble a staple. Fusion device 1200 may be described as an anchor clip. Anchor clip 1200 may include a first anchor arm 1202, a second anchor arm 1204 and a central beam 1206 that is located between the first anchor arm and the second anchor arm. The central arm 1206 may have some degree of curvature, or may be a straight beam that lies between the two arms 1202, 1204. FIG. 8A shows an example in which an axis that extends the length of the central arm 1206 may be perpendicular to an axis that extends the length of the first anchor arm 1202 and an axis that extends the length of the second anchor arm 1204. Other angular arrangements are contemplated. For example, the axes of the arms 1202, 1204 may converge or diverge. The surfaces of the first arm 1202 and second arm 1204 may be smooth, or may be textured, for example, they may include roughening, ridges, teeth or blades to enhance fixation in the bone. The arms 1202, 1204 may also include a sharpened tip 1208 to facilitate insertion of the arm into a bone or other tissue. The first arm 1202 and second arm 1204 may also include at least one aperture 1210. Aperture 1210 may contain and/or distribute bone graft, biologics, or growth factors. Aperture 1210 may also provide a fenestration for bone ingrowth, or for imaging of the developing fusion mass.

Figure 9:
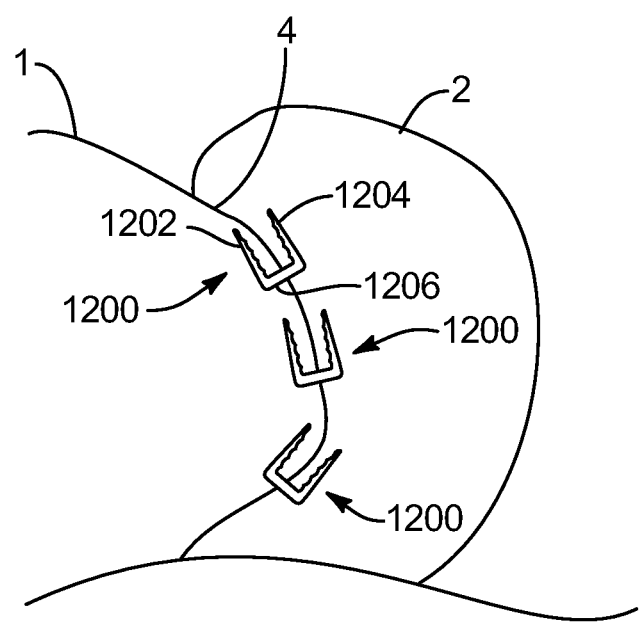
FIG. 9 is an anterior-posterior view of portions of a sacrum and ilium, with several fusion devices of FIG. 8A implanted along the sacroiliac joint, each device oriented in an anterior-posterior direction.

Referring to FIG. 9, the anchor clip 1200 may be inserted such that the axis of the central beam 1206 intersects the sacroiliac joint 4 and extends across the joint. The first arm 1202 may be embedded within the sacrum 1 and the second arm 1204 may be embedded within the ilium 2, or vice versa. Multiple anchor clips 1200 may be inserted adjacent to one another along the length of the joint 4, as shown.

Figure 11A:
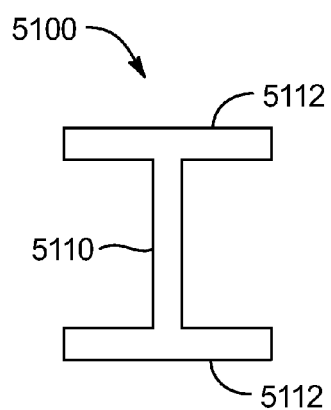
FIG. 11A is an end view of yet another fusion device.
Figure 11B:
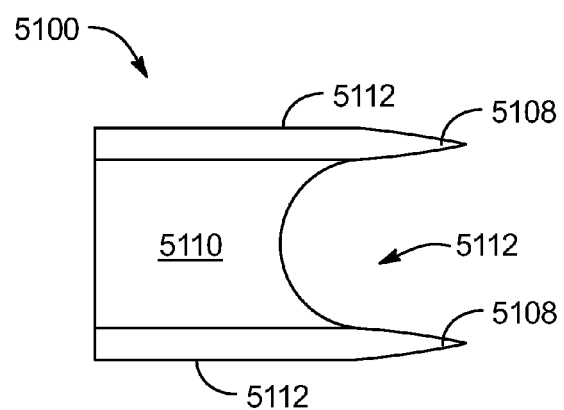
FIG. 11B is a side view of the fusion device of FIG. 11A.

Referring to FIG. 11A, yet another example of a fusion device 5100 may resemble the fusion device 1200, at least in some characteristics. Fusion device 5100 may include a pair of blades 5112 extending from opposite ends of a central arm 5110 or web, so that an end view of the device 5100 may resemble an I-beam. The blades 5112 may be perpendicular to the arm 5110, as shown in FIG. 11A, or may be oriented at an obtuse or acute angle. The blades 5112 may include sharpened, pointed tips 5108 on a leading end of the device 5100. The arm 5110 may extend the full length of the device 5100, or may extend only partially along the length. An arrangement with a partial length arm 5110 may resemble fusion device 1200. The arm 5110 may include a recess 5112 at the leading end of the device. The recess 5112 may be described as a concave indentation. The leading edge of the recess 5112 may be sharpened to better cut through bone as the device 5100 is inserted. Any of the fusion devices disclosed herein may have sharpened leading edges for this purpose.

Figure 12:
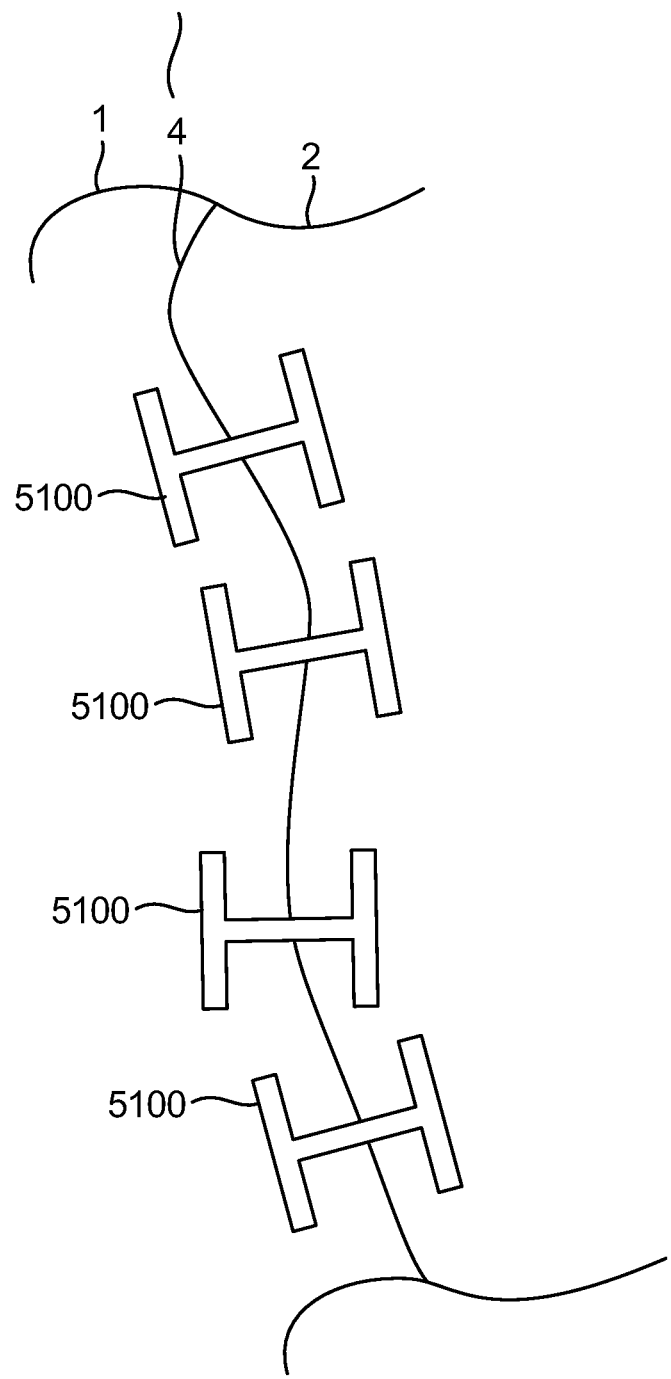
FIG. 12 is an anterior-posterior view of portions of a sacrum and ilium, with several fusion devices of FIG. 11A implanted along the sacroiliac joint, each device oriented in an anterior-posterior direction.

Referring to FIG. 12, one or more devices 5100 may be implanted from an anterior or posterior approach so that the arm 5110 extends across a sacroiliac joint line 4, a first blade 5112 is in the sacrum 1, and a second blade 5112 is in the ilium 2. This arrangement may provide compression across the joint due, for example, to divergent blade tips 5108 or other adaptations. FIG. 12 illustrates several devices 5100 in a curved arrangement that generally follows the joint line 4, similar to the arrangements shown in FIGS. 7 and 9.

Figure 13:
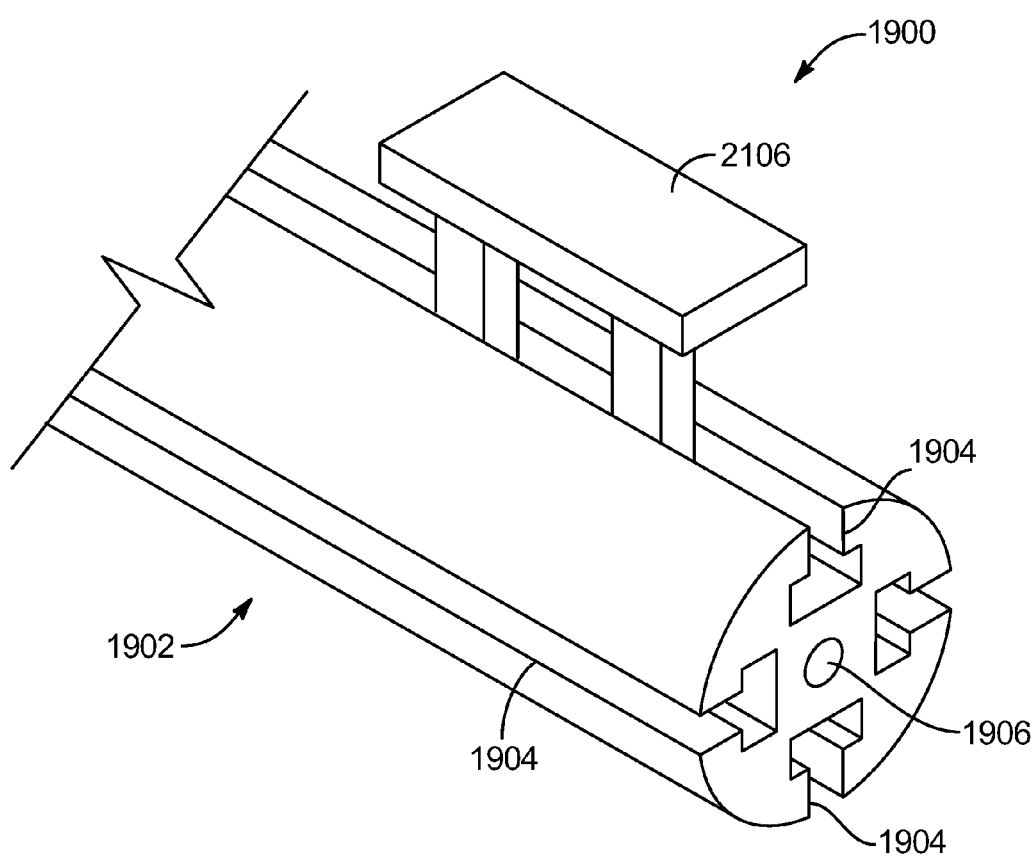
FIG. 13 is a side oblique view of a portion of a tool for inserting blade anchors into fusion devices.

Referring to FIG. 13, a tool 1900 for inserting a fusion device may include a working portion 1902 which may be shaped and sized to match a particular cage geometry, or at least a cross sectional geometry of a cage. The working portion 1902 in FIG. 13 is cylindrical to match a cylindrical cage, such as cage 1102, 2102, 3102, 4102, or 1300. The working portion 1902 may also include one or more dovetail slots 1904, which may correspond to the number and spacing of the dovetail slots in a particular cage. The dovetail slots 1904 in FIG. 13 are arranged to resemble the slots 2104 of cage 2102 or the slots 3104 of cage 3102. The slots 1904 may be the same size and shape as the slots of a cage, or may provide more or less clearance with the corresponding connecting feature of an anchor. The working portion 1902 may also include a cannulation 1906, which may be centrally located. The tool 1900 may also include a shaft portion (not shown) and/or a handle portion (not shown) serially connected to the working portion.

In use, the tool 1900 may be connected to a cage, such as cage 2102 for example. A threaded rod (not shown) may be inserted through cannulation 1906 and threaded into a socket in cage 2102 to connect the tool to the cage. The tool and/or cage may have additional complementary features to ensure that the slots 2104 line up with the slots 1904 and stay aligned throughout use. An anchor 2106 is loaded into each slot 1904, such as by sliding the anchor 2106 axially into the slot 1904. The anchor 2106 is advanced along the slot 1904 and then along slot 2104 until the anchor is fully seated in the cage 2102. Multiple anchors may be inserted sequentially or simultaneously. The tool 1900 may then be removed from the cage 2102. The threaded rod may be unthreaded to release the connection between the tool and the cage.

Figure 14:
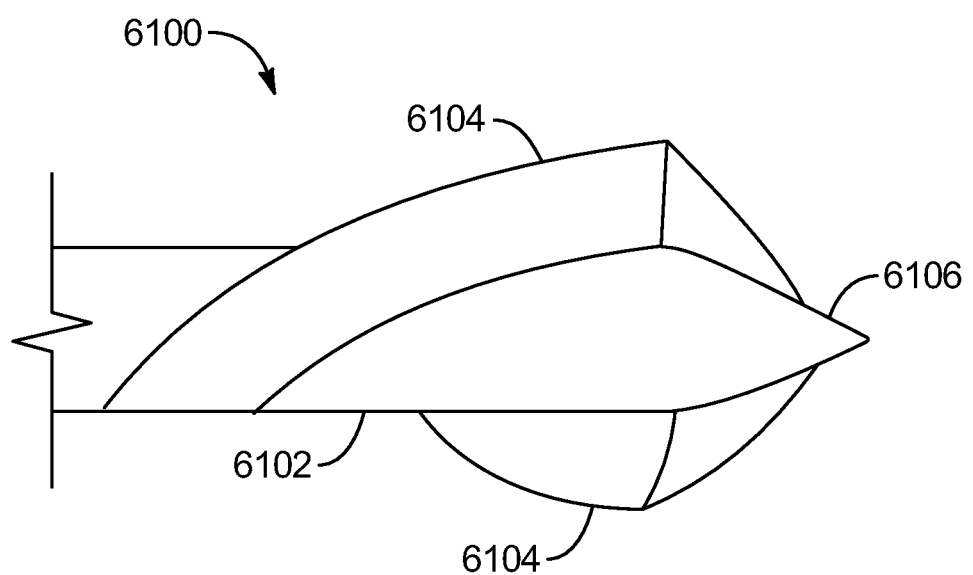
FIG. 14 is a side view of yet another fusion device.
Figure 15:
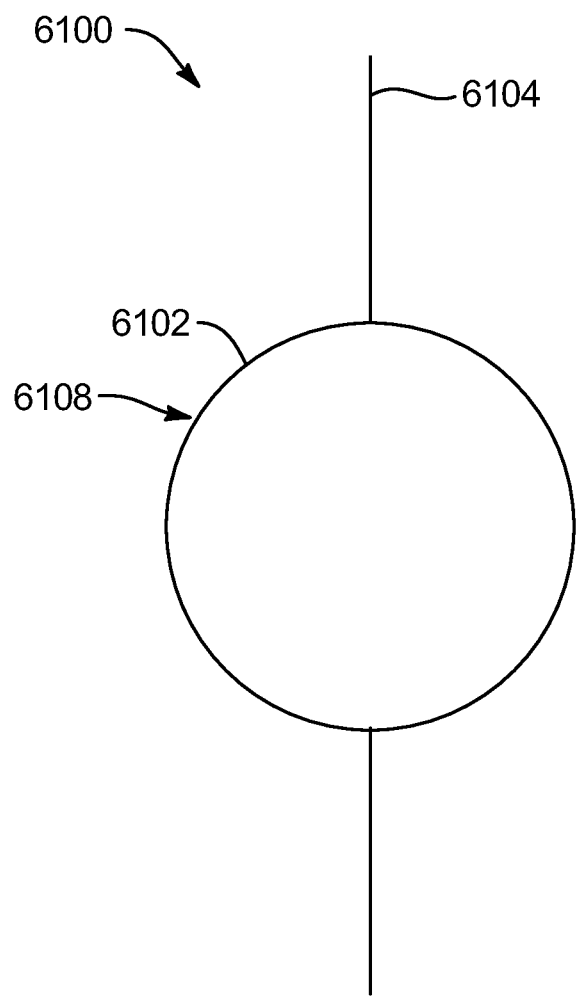
FIG. 15 is an end view of the fusion device of FIG. 14.

Referring to FIG. 14, yet another fusion device 6100 may include an elongated shaft 6102 with one or more helical fins 6104 protruding outwardly from the shaft 6102. FIG. 14 illustrates an example which has two fins 6104 on opposite sides of the shaft 6102. The helical fins may make few revolutions around the shaft; in some examples, as in FIG. 14, each fin may make less than one full revolution around the shaft. The shaft may have a pointed leading end 6106. The fins 6104 may taper in this region as well. With reference to FIG. 15, shaft 6102 may include a cannulation 6108 through its entire length.

Figure 16:
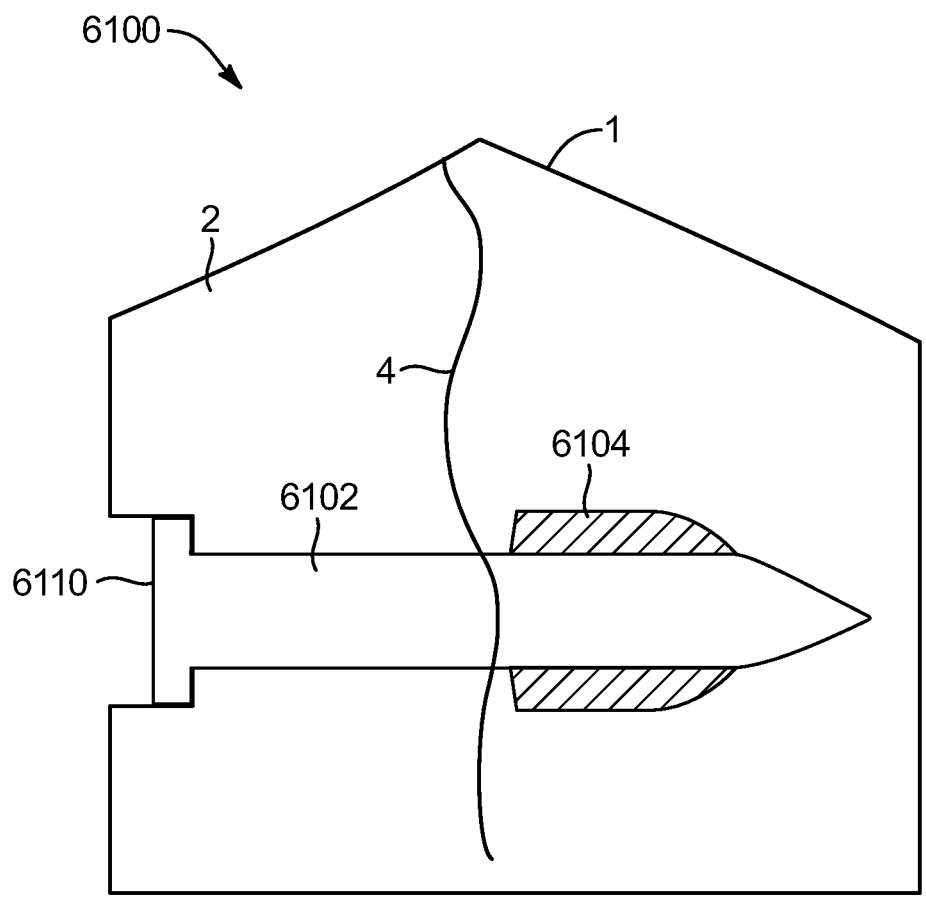
FIG. 16 is an anterior-posterior view of portions of a sacrum and ilium, with the fusion device of FIG. 14 implanted across the sacroiliac joint in a medial-lateral direction.

In use, the fusion device 6100 may be inserted into bone by twisting, pushing, or impacting. As the fusion device 6100 advances and the helical fins 6104 engage the bone, the fusion device 6100 may rotate either on its own or due to the insertion method. The twisting action may induce compression between bones or bone fragments. The helical fins 6104 may also provide an anti-back-out action. FIG. 16 illustrates an example in which device 6100 has been inserted through an ilium 2, across a sacroiliac joint line 4, and into a sacrum 1. FIG. 16 also shows that device 6100 may include a head 6110, which may be received in a counterbored socket in a bone or fragment.

Figure 17:
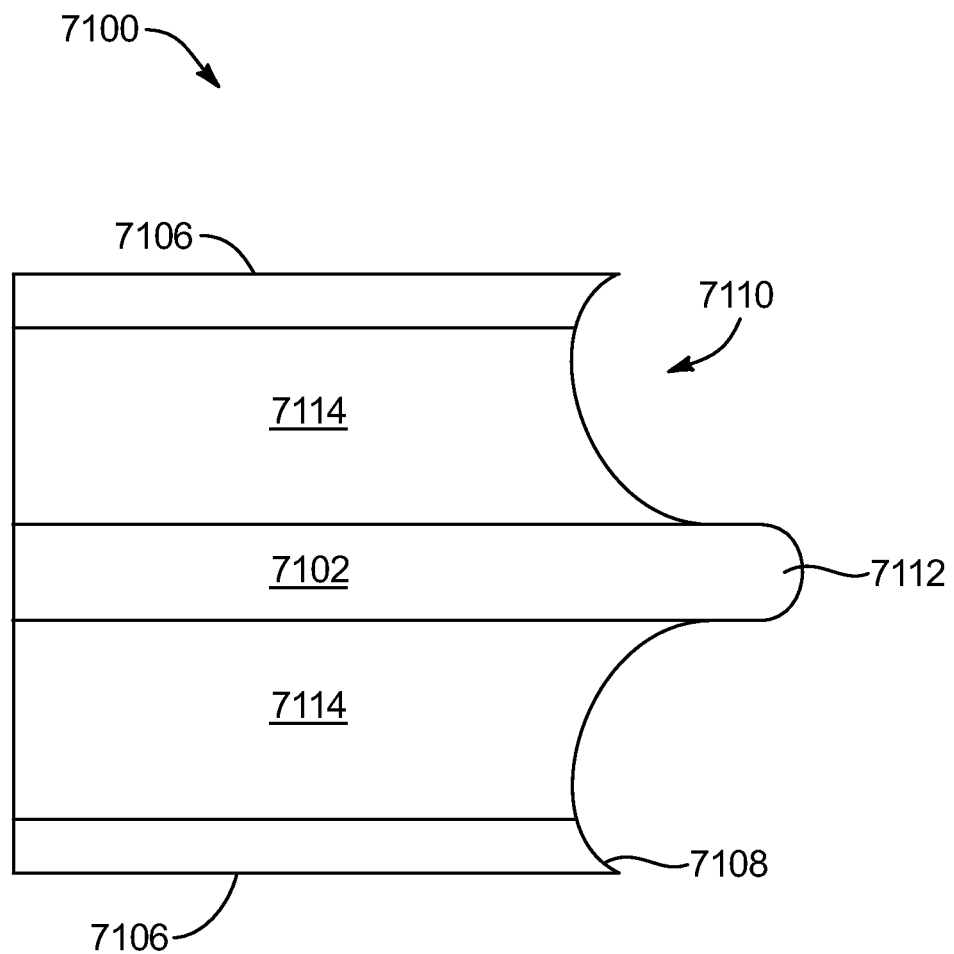
FIG. 17 is a side view of yet another fusion device.
Figure 18:
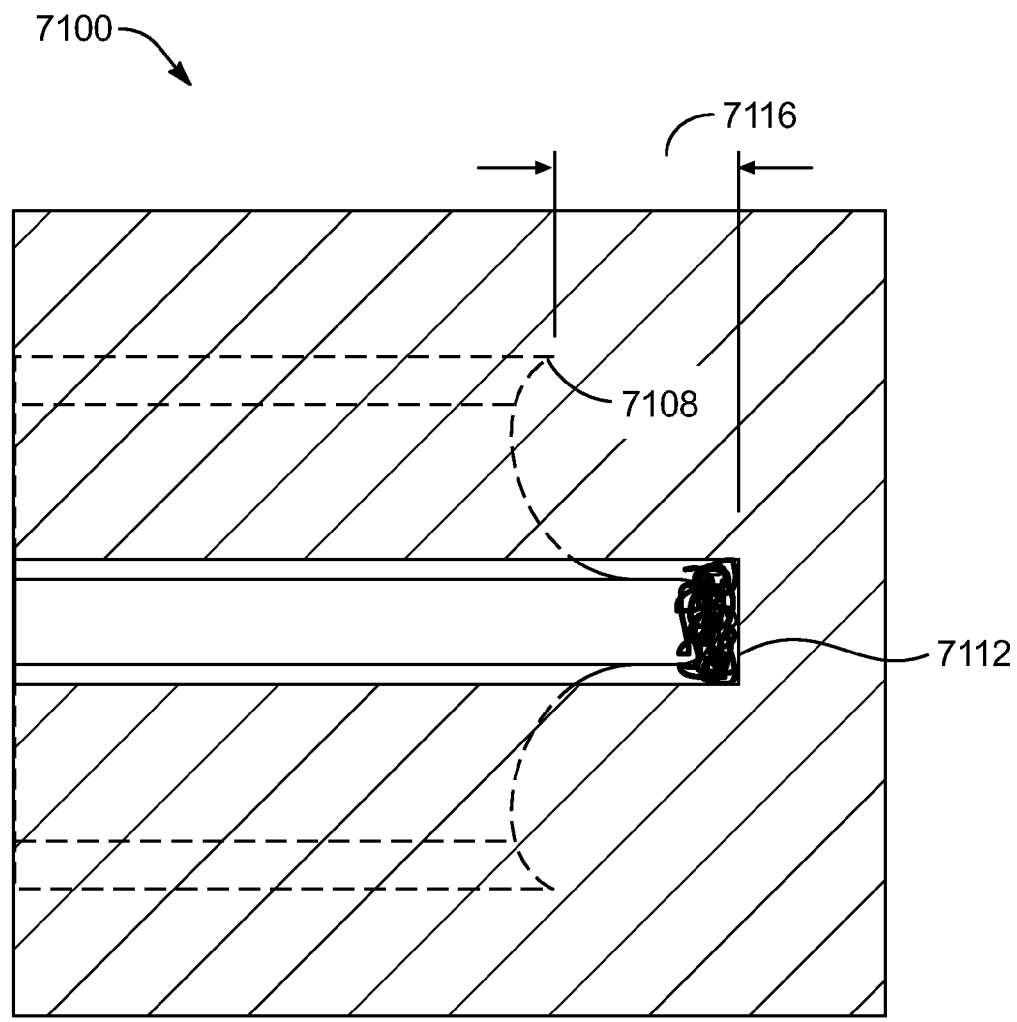
FIG. 18 is a side view of the fusion device of FIG. 17 inserted into bone.

FIG. 17 illustrates yet another fusion device 7100, which includes a generally cylindrical pin 7102 and two anchor blades 7106 on opposite sides of the pin. The anchor blades 7106 may include sharpened leading tips 7108 for cutting through bone. An arm 7114 or web may extend between the central pin 7102 and each anchor blade 7106. Leading edges 7110 of the arms 7114 may also be sharpened. The leading tip 7112 of the pin 7102 may extend past the leading tips 7108 of the blades 7106, as indicated by dimension 7116 in FIG. 18. An end view (not shown) of the device 7100 may resemble the Greek capital letter phi. This example illustrates that anchors may be integrally formed with the central pin. This example may be viewed as an integrally formed version of the example shown in FIG. 5.

Figure 19:
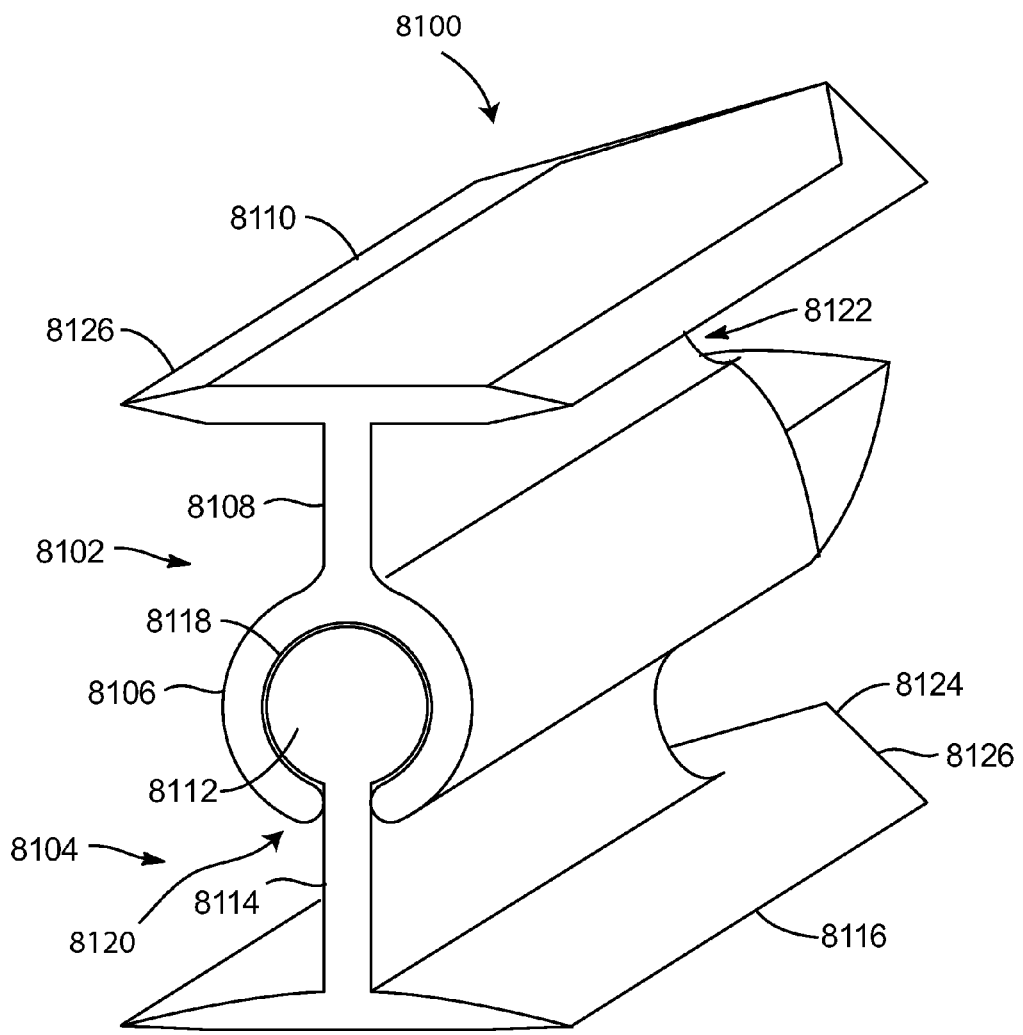
FIG. 19 is an oblique view of yet another fusion device.

FIG. 19 illustrates yet another fusion device 8100 which may be considered a modular form of the device of FIG. 17. Device 8100 includes a first component 8102 and a second component 8104.

The first component 8102 includes a body 8106, an arm 8108 or web, and a blade 8110. The body 8106 may be a generally cylindrical feature that extends more or less the full length of the device 8100. The body 8106 may include a central hole 8118 which may be full length. The body 8106 may also include a full length slot 8120 which communicates with the hole 8118 to form an undercut slot similar to those described elsewhere in this disclosure. The arm 8108 extends between the body 8108 and the blade 8110. A leading edge 8122 of the arm may be concave and sharpened. The blade 8110 extends transverse or oblique to the arm 8108 and may have a sharpened leading tip 8124 and/or edges 8126.

The second component 8104 includes a body 8112, an arm 8114 or web, and a blade 8116. The body 8112 may be a cylindrical feature that extends more or less the full length of the device 8100. The body 8112 has an outer diameter which is equal to or less than the inside diameter of the hole 8118. The arm 8114 extends between the body 8112 and the blade 8116. The arm 8114 may be equal to or narrower than the width of the slot 8120. A leading edge 8122 of the arm may be concave and sharpened. The blade 8116 extends transverse or oblique to the arm 8114 and may have a sharpened leading tip 8124 and/or edges 8126.

Figure 20:
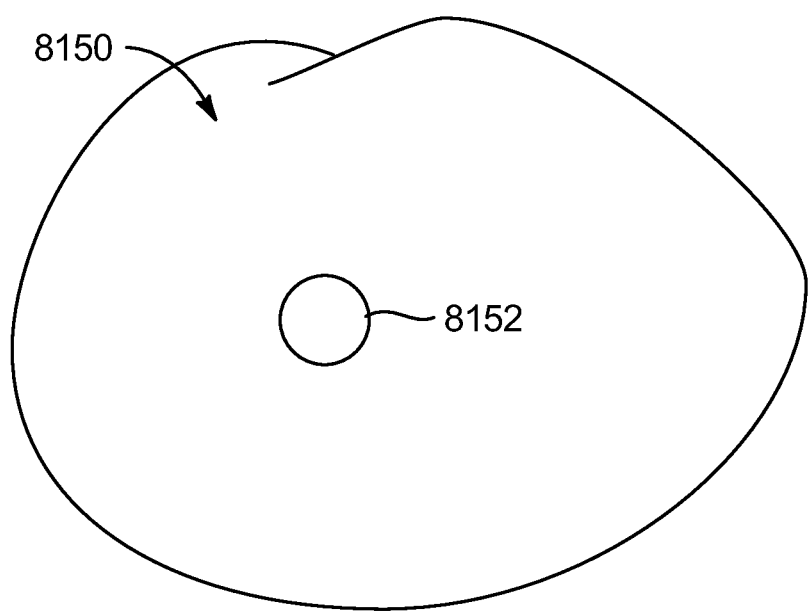
FIG. 20 is an end view of a bone tunnel and a guide wire extending into the bone tunnel.

FIG. 20 is an end view of a bone tunnel 8150 to receive body 8106. A guide wire 8152 is in the center of the tunnel 8150. In a method of use, the guide wire 8152 may be inserted into bone to establish a desired trajectory for the device 8100. A drill (not shown) may then be used to create the tunnel 8150. The first component 8102 may be inserted into the bone along the trajectory so that the body 8106 is coaxial with the tunnel 8150. This may be accomplished, for example, by using an inserter tool (not shown) which includes a portion that may mimic the size and shape of body 8112 and arm 8114, and may include a cannulation to receive the guide wire 8152. This portion of the inserter tool may be inserted into the hole 8118 and slot 8120, and the tool and component 8102 advanced together over the guide wire 8152 until the component 8102 is fully seated. The arm 8108 and blade 8110 may cut through bone, or may follow a pre-cut path through bone. The inserter tool may be withdrawn, and the second component may be inserted into the bone along the trajectory so that the body 8112 and arm 8114 are received in the hole 8118 and slot 8120. This example may provide for some amount of angular adjustment between the first and second components due to the cylindrical mating interface.

Figure 21:
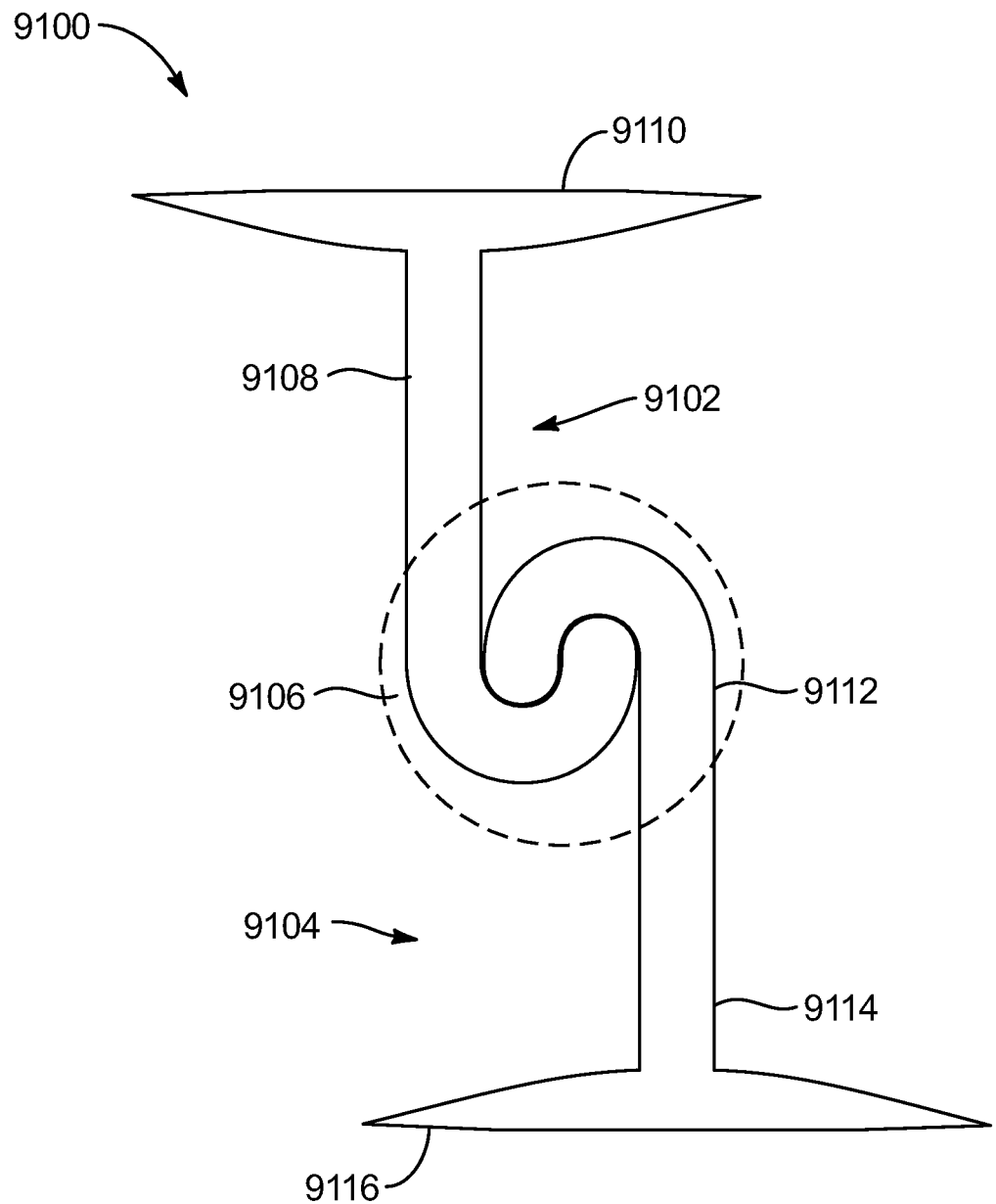
FIG. 21 is an end view of yet another fusion device.

FIG. 21 illustrates yet another fusion device 9100. This example is a two-part device with a first component 9102 and a second component 9104. The first and second components may share some of the characteristics of the preceding example of FIG. 19, with the exception that device 9100 includes a different interconnection.

The first component 9102 includes a body 9106, an arm 9108 or web, and a blade 9110. In this example, the body 9106 forms a channel beside the arm 9108. The body 9106 may be described as a recurved or bent portion of the arm 9108.

The second component 9104 includes a body 9112, an arm 9114 or web, and a blade 9116. The body 9112 is shaped like body 9106.

The first and second components 9102, 9104 may be connected by hooking the bodies 9106, 9112 together along more or less the entire length of the device 9100. This example may also afford some angular adjustment between the first and second components 9102, 9104 as a consequence of the interconnection.

Figure 22:
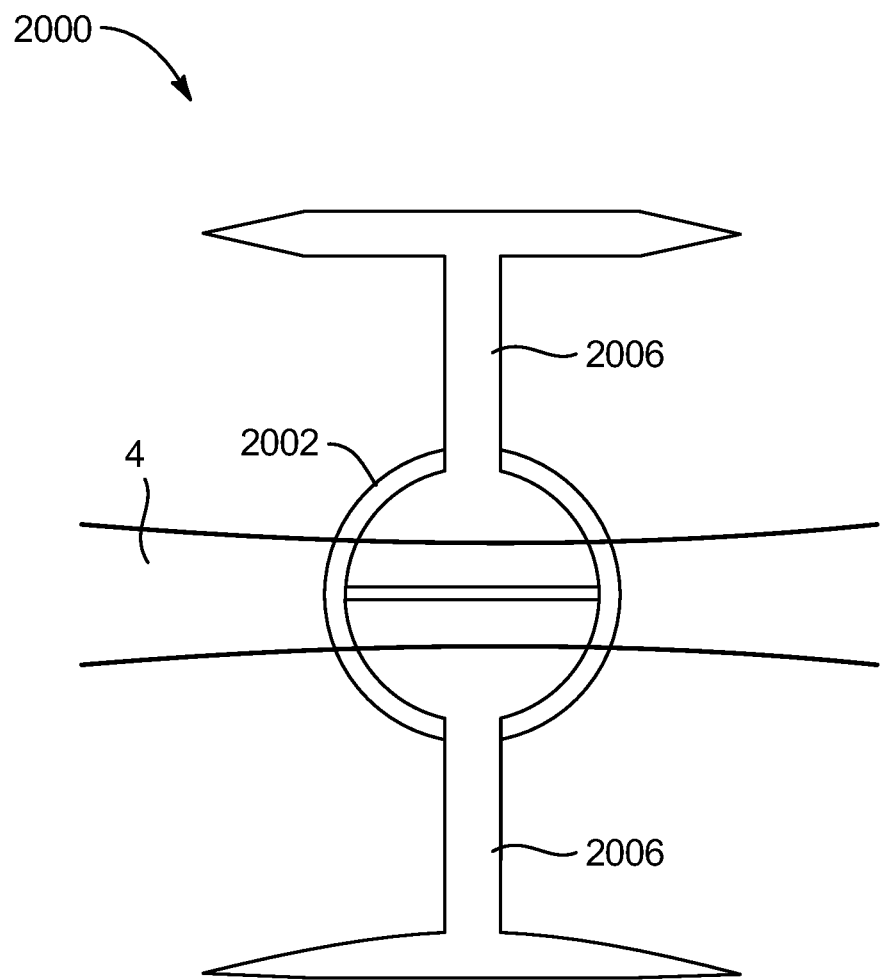
FIG. 22 is an end view of yet another fusion device implanted across a joint line.
Figure 23:
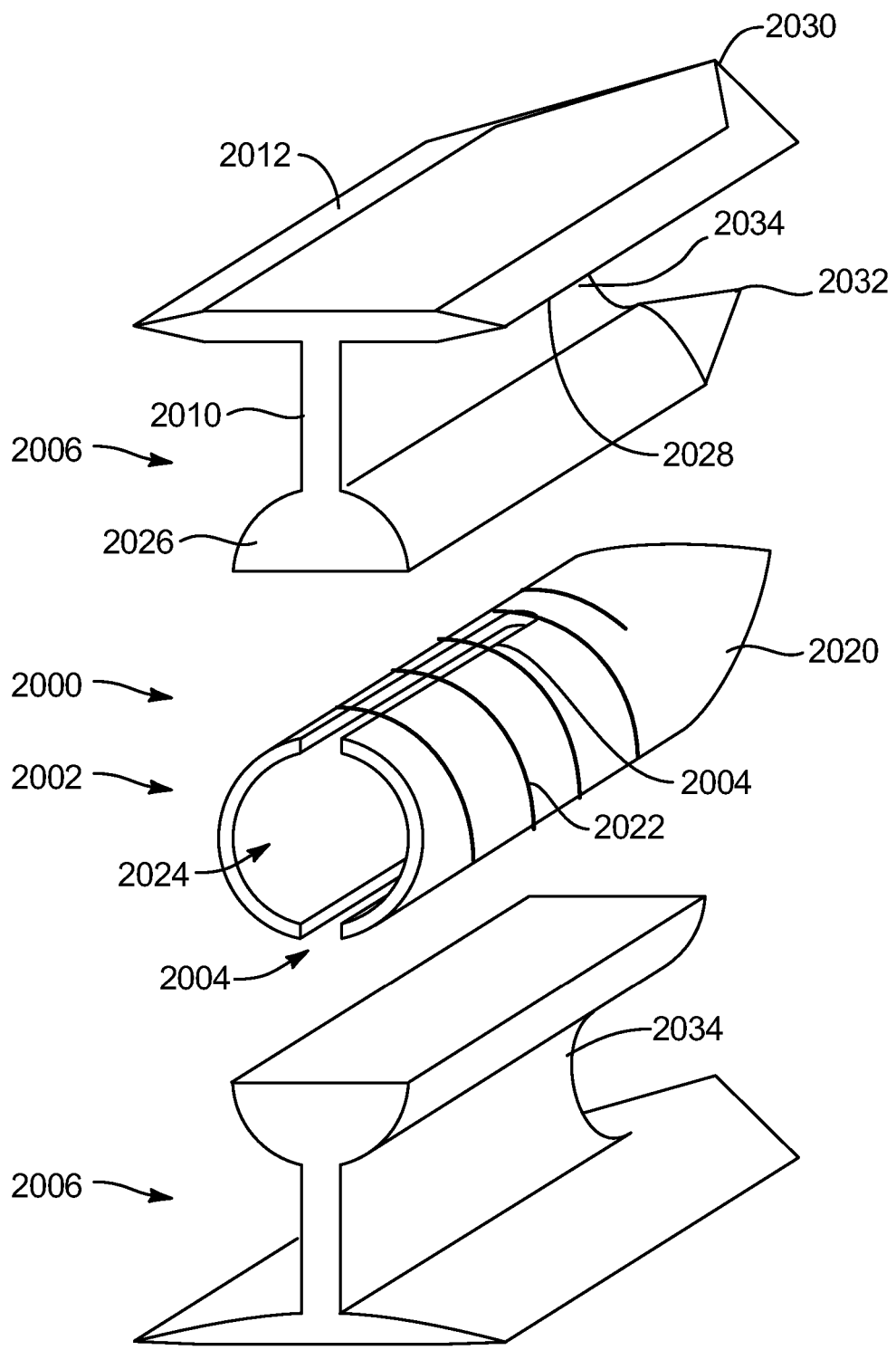
FIG. 23 is an oblique exploded view of the fusion device of FIG. 22.

FIG. 22 illustrates yet another fusion device 2000 implanted across a sacroiliac joint line 4. This example is a three-part device with a cage 2002 and two anchors 2006. The cage 2002 is cylindrical and includes two opposing slots 2004 which communicate with an internal bore 2024. A leading end 2020 of the cage may be tapered. The cage 2002 may include external threads 2022, ridges, teeth, or the like to enhance fixation. Each anchor includes an arm 2010, a blade 2012 along an edge of the arm and extending transverse to the arm, and a fixation feature 2026 extending along an opposite edge of the arm. The arm may have a concave and/or sharpened leading edge 2034. Leading and/or side edges 2028 of the blade 2012 may be sharpened, and the blade may include a sharpened tip 2030. The fixation feature 2026 in this example is a semicircular enlargement. The fixation feature 2026 may include a tapered or sharpened tip 2032.

Figure 24:
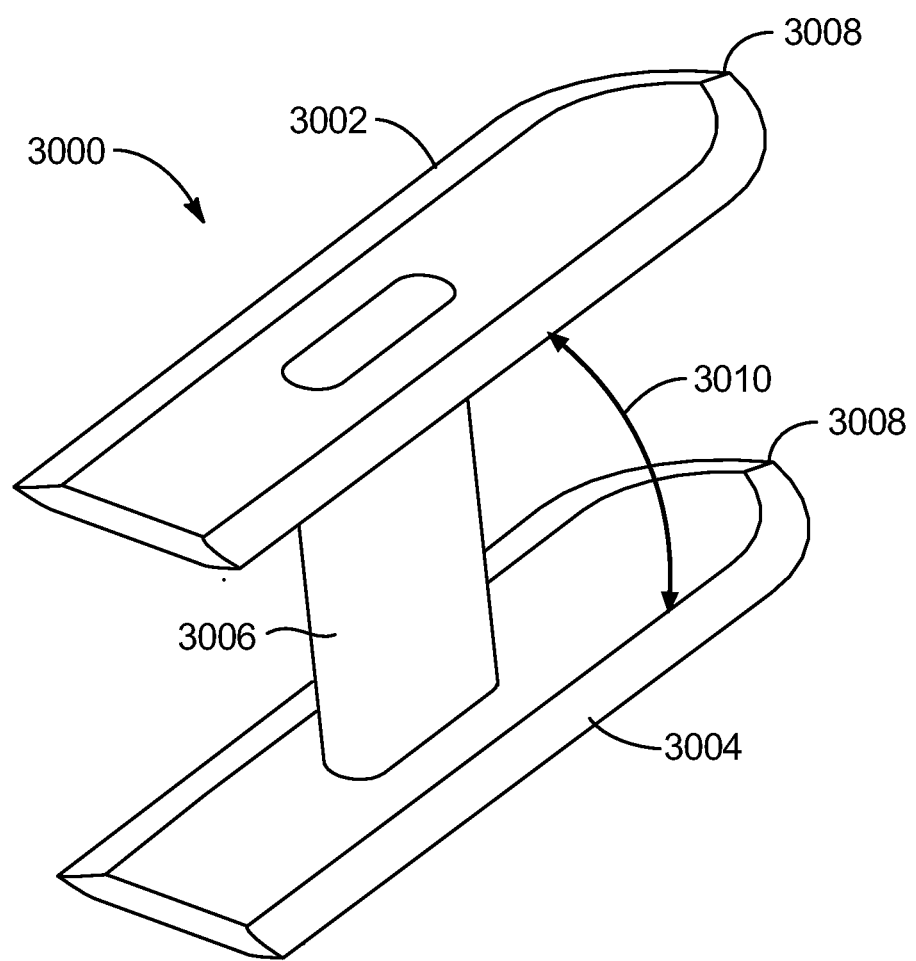
FIG. 24 is an oblique view of yet another fusion device.

FIG. 24 illustrates yet another fusion device 3000, which may be monolithically formed or permanently assembled, such as by welding. Device 3000 includes a first arm 3002, a second arm 3004, and a beam 3006 between the arms 3002, 3004. The arms may be wedge shaped in at least one view so that each arm has a tapered or sharpened leading tip 3008. Other leading or side edges may also be sharpened as described for other examples. The arms 3002, 3004 may also be oriented with an acute angle 3010 between them so that the tips 3008 are farther apart than the opposite ends of the arms 3002, 3004.

Figure 25:
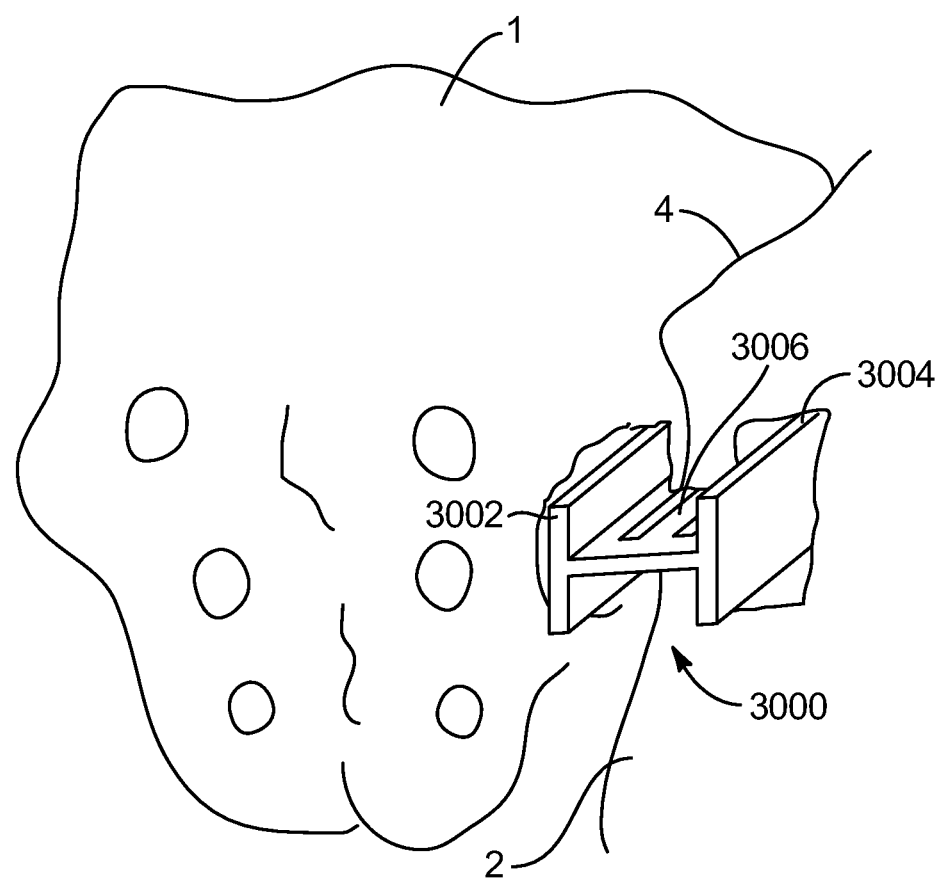
FIG. 25 is a posterior view of portions of a sacrum and ilium, with the fusion device FIG. 24 partially inserted from a posterior approach across a sacroiliac joint line.

FIG. 25 illustrates device 3000 partially inserted into bone along an anterior-posterior trajectory, or a posterior approach. One arm 3002 is partially inserted into a sacrum 1, the other arm 3004 is partially inserted into an ilium 2, and the beam 3006 extends across the sacroiliac joint line 4.

Figure 26:
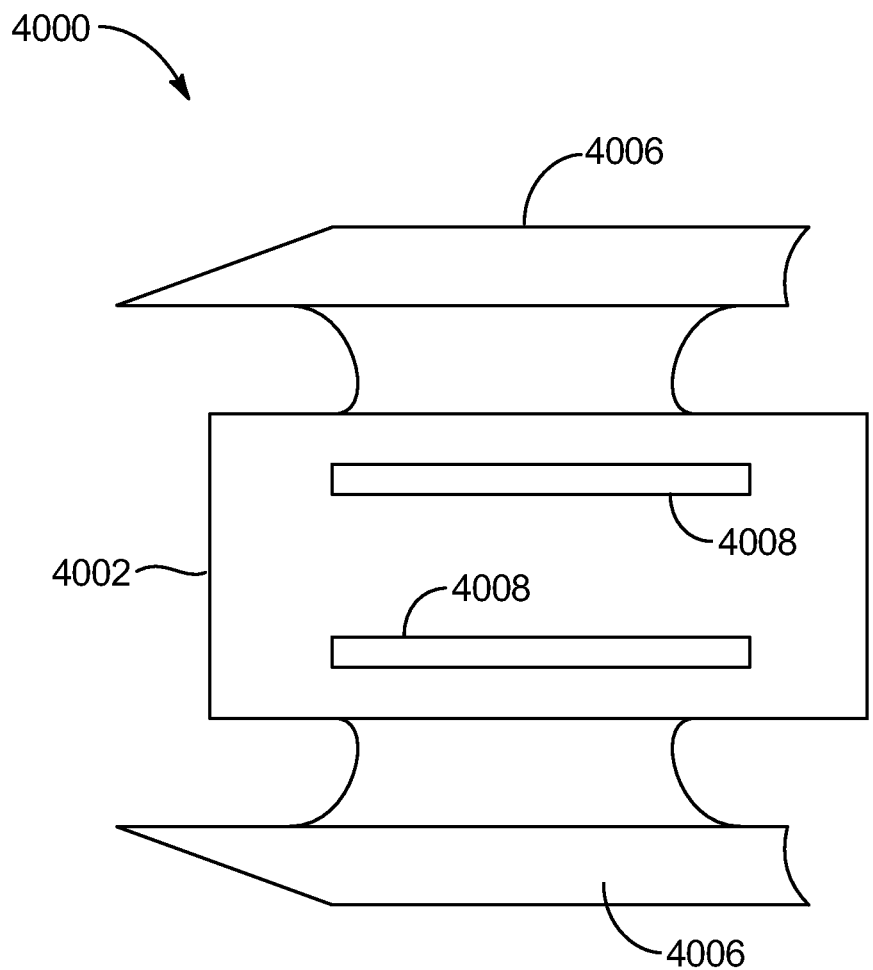
FIG. 26 is a side view of yet another fusion device.
Figure 27:
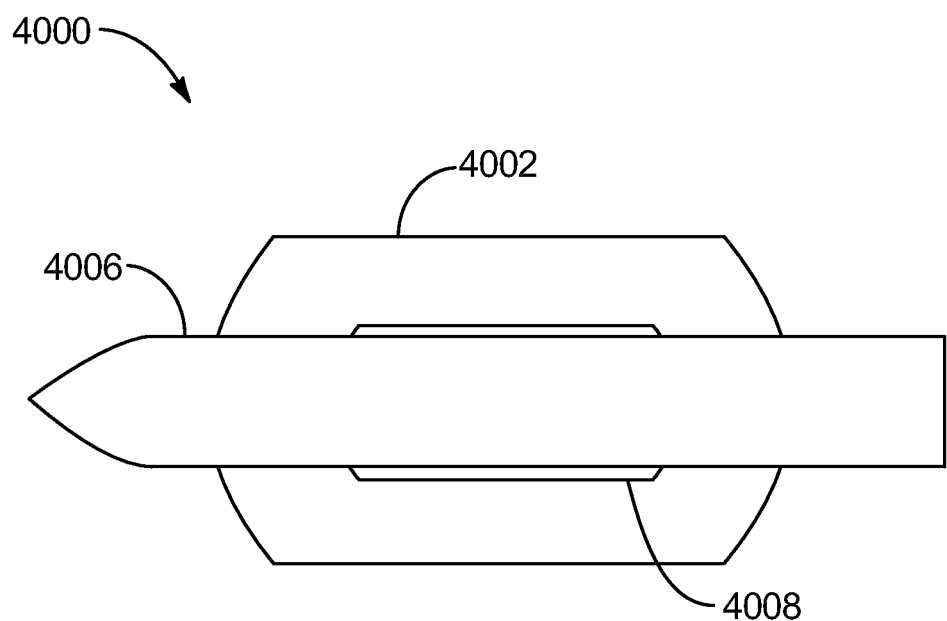
FIG. 27 is a view of the fusion device of FIG. 26.
Figure 28:
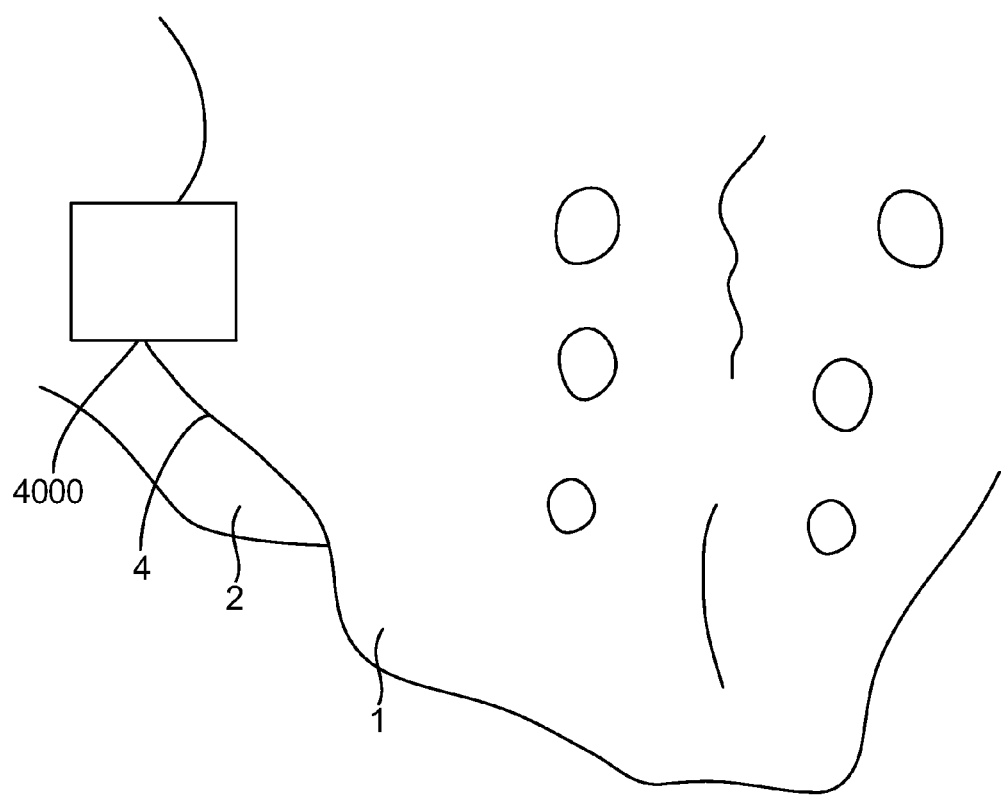
FIG. 28 is a posterior view of portions of a sacrum and ilium, with the fusion device of FIG. 26 inserted from a posterior approach across a sacroiliac joint line.

FIG. 26 illustrates yet another fusion device 4000. Similar to other examples herein, device 4000 is illustrated with two anchors 4006 extending from opposite sides of a cage 4002. Fusion device 4000 may carry bone graft material or other therapeutic agents in recesses 4008 in the cage 4002 or anchors 4006, as shown in FIGS. 26-27. FIG. 28 is a posterior view showing device 4000 implanted across a sacroiliac joint line 4.

Figure 29:
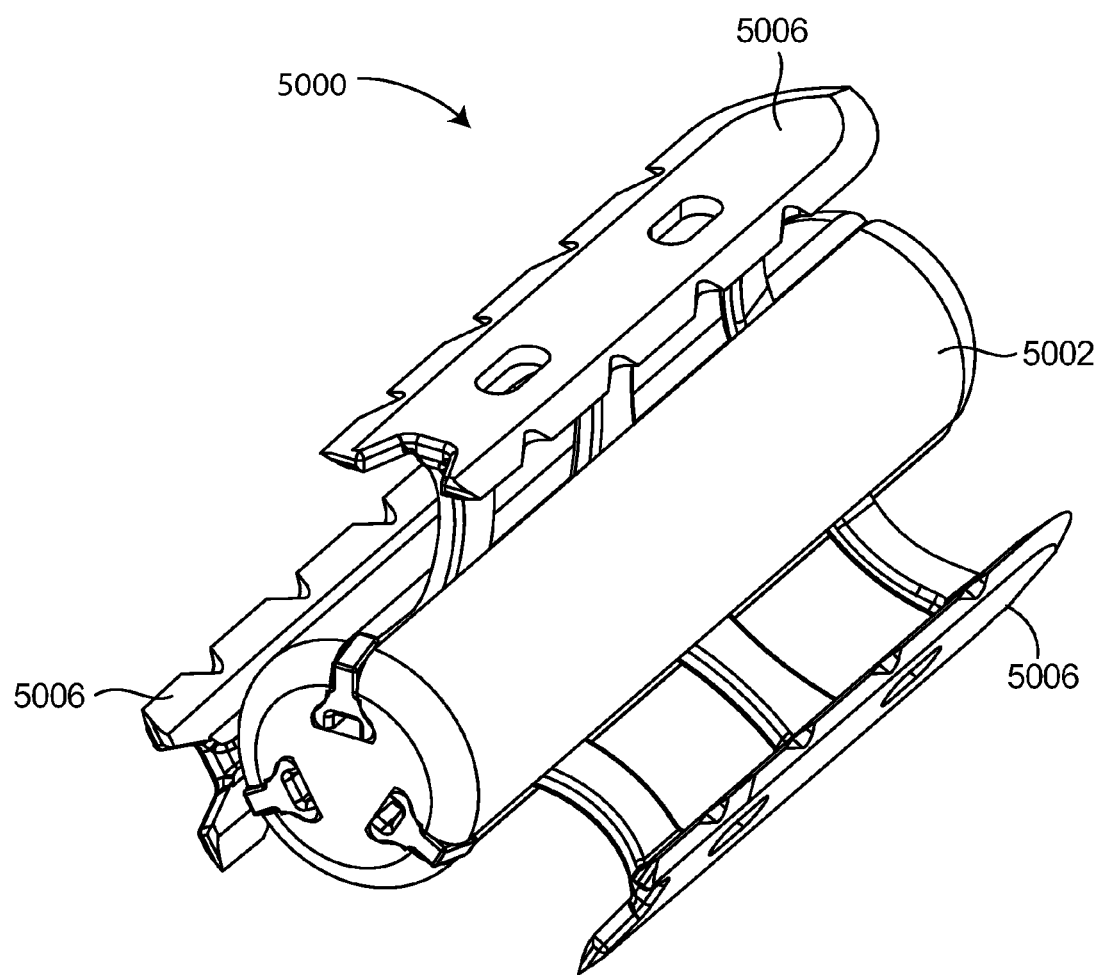
FIG. 29 is an oblique view of yet another fusion device.
Figure 30:
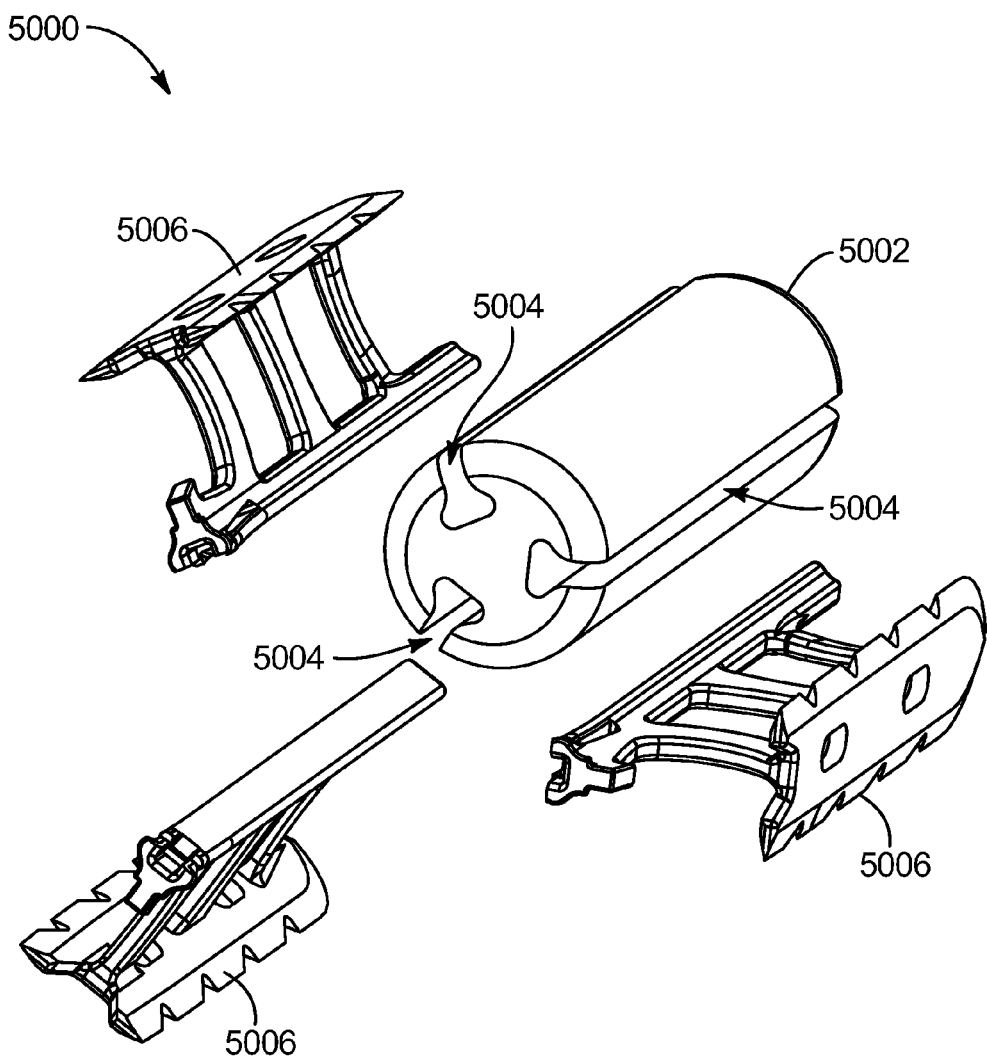
FIG. 30 is an oblique exploded view of the fusion device of FIG. 29.
Figure 31:
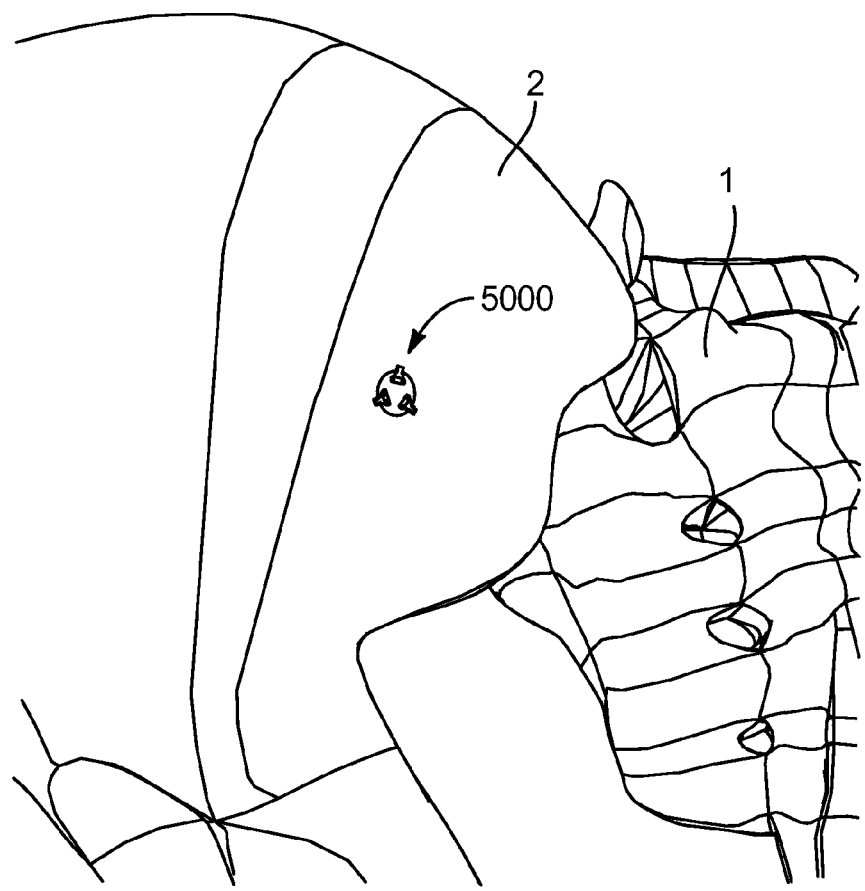
FIG. 31 is a postero-lateral view of portions of a sacrum and ilium, with the fusion device of FIG. 29 implanted from a postero-lateral approach.

FIG. 29 illustrates yet another fusion device 5000, which includes a cylindrical cage 5002 with three dovetail slots 5004 evenly spaced around a generally circular perimeter, and three anchors 5006. FIG. 30 is an exploded view of the device 5000.

The present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, a blade configuration from one or more fixation device examples may be found on the other fixation device examples disclosed herein. Similarly, manufacturing, assembly or implantation methods described for one fixation device or component may be used in the manufacture, assembly or implantation of the other fixation devices or components disclosed herein. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for sacroiliac joint fusion, the method comprising:

establishing an implant trajectory that passes through the sacroiliac joint;

forming a tunnel along the implant trajectory, wherein an iliac portion of the tunnel passes through an iliac bone, wherein a sacral portion of the tunnel passes through a sacral bone; and inserting an elongated body of a fusion device along the implant trajectory so that an iliac portion of the fusion device is positioned in the iliac portion of the tunnel and a sacral portion of the fusion device is positioned in the sacral portion of the tunnel, the fusion device extending longitudinally between a proximal end and a distal end, the proximal end of the fusion device being a trailing side and the distal end being a leading side of the fusion device, the elongated body of the fusion device extending longitudinally to exhibit an elongated cylindrical structure having blunt opposite ends, the elongated cylindrical structure of the fusion device defining a plurality of slots each extending axially along a longitudinal axis of the fusion device such that each of the plurality of slots extend from the proximal end of the fusion device;

wherein the fusion device comprises a plurality of anchors extending beyond the tunnel, each of the plurality of anchors including a base portion, an arm portion and a blade portion such that the base portion of each of the plurality of anchors is insertable through and along one of the plurality of slots, the plurality of anchors configured to cut through a wall of the tunnel.

2. The method of claim 1, wherein forming the tunnel comprises cutting through the sacrum and ilium with the fusion device.

3. The method of claim 1, wherein inserting the fusion device comprises inserting the elongated body of the fusion device into the tunnel, inserting a first anchor of the plurality of anchors into the elongated body so that a portion of the anchor extends through the wall of the tunnel, and inserting a second anchor of the plurality of anchors into the elongated body so that a portion of the second anchor extends through the wall of the tunnel.

4. The method of claim 1, comprising inserting a second fusion device along a second implant trajectory so that the second fusion device engages iliac and sacral bone.

5. The method of claim 1, wherein inserting the fusion device comprises compressing the ilium and the sacrum together with the fusion device.

6. A method for sacroiliac joint fusion, the method comprising:

establishing an implant trajectory that passes through the sacroiliac joint;

forming a tunnel along the implant trajectory, wherein an iliac portion of the tunnel passes through an iliac bone, wherein a sacral portion of the tunnel passes through a sacral bone;

inserting an elongated body of a fusion device along the implant trajectory so that an iliac portion of the fusion device is positioned in the iliac portion of the tunnel and a sacral portion of the fusion device is positioned in the sacral portion of the tunnel, the fusion device extending between a proximal end and a distal end, the proximal end of the fusion device being a trailing end and the distal end being a leading end of the fusion device, the elongated body of the fusion device extending longitudinally to exhibit an elongated cylindrical structure having blunt opposite ends, the elongated cylindrical structure of the fusion device defining a first slot and a second slot each extending axially along a longitudinal axis of the fusion device and extending from the proximal end of the fusion device; and upon the elongated body being inserted within the tunnel, inserting a first anchor of the fusion device along the first slot of the elongated body so that the first anchor cuts through a wall of the tunnel, and inserting a second anchor of the fusion device along the second slot of the elongated body so that the second anchor cuts through the wall of the tunnel.

7. The method of claim 6, further comprising inserting a third anchor of the fusion device along a third slot defined in the fusion device such that the third anchor is forced to slide along the third slot and so that the third anchor cuts through the wall of the tunnel.

8. The method of claim 6, wherein forming the tunnel comprises cutting through the sacrum and ilium with the fusion device.

9. The method of claim 6, further comprising inserting a second fusion device along a second implant trajectory so that the second fusion device engages iliac and sacral bone.

10. The method of claim 6, wherein inserting the fusion device comprises compressing the ilium and the sacrum together with the fusion device.

11. The method of claim 7, wherein the inserting each of the first anchor, the second anchor, and the third anchor comprises positioning each of the first blade, the second blade, and a third blade to extend in a first plane, a second plane, and a third plane, respectively, such that each of the first plane, the second plane, and the third plane are transverse relative to each other.

12. The method of claim 6, wherein the inserting the elongated body comprises inserting the elongated body including the first slot, the second slot, and a third slot defined in the elongated body so as to be evenly spaced relative to each other within a periphery of the elongated body.

13. The method of claim 6, wherein the inserting the elongated body comprises inserting the elongated body including the first slot, the second slot, and a third slot so as to be radially symmetric relative to the longitudinal axis.

14. A method for sacroiliac joint fusion, the method comprising:

establishing an implant trajectory that passes through the sacroiliac joint;

forming a tunnel along the implant trajectory, wherein an iliac portion of the tunnel passes through an iliac bone, wherein a sacral portion of the tunnel passes through a sacral bone;

inserting an elongated body of a fusion device along the implant trajectory so that an iliac portion of the fusion device is positioned in the iliac portion of the tunnel and a sacral portion of the fusion device is positioned in the sacral portion of the tunnel, the fusion device extending longitudinally between a proximal end and a distal end, the proximal end of the fusion device being a trailing end and the distal end being a leading end of the fusion device, the elongated body of the fusion device extending longitudinally to exhibit an elongated cylindrical structure having blunt opposite ends, the elongated cylindrical structure of the fusion device defining a first slot and a second slot each extending axially along a longitudinal axis of the fusion device and extending from the proximal end of the fusion device; and upon the elongated body being positioned within the tunnel, forcing a first blade and a first arm portion of a first anchor of the fusion device to cut through a wall of the tunnel with a first base of the first anchor inserted along the first slot of the elongated body, and forcing a second blade and a second arm portion of a second anchor of the fusion device to cut through the wall of the tunnel with a second base of the second anchor inserted along the second slot of the elongated body.

15. The method of claim 14, further comprising inserting a second fusion device along a second implant trajectory so that the second fusion device engages iliac and sacral bone.

16. The method of claim 14, wherein inserting the fusion device comprises compressing the ilium and the sacrum together with the fusion device.

17. The method of claim 14, wherein the forcing each of the first blade and the second blade comprises forcing a third anchor with a third blade along a third slot of the fusion device such that the first blade, the second blade, and the third blade extend in transverse planes relative to each other.

\* \* \* \* \*